United States Patent
Takahashi et al.

(10) Patent No.: US 10,626,368 B2
(45) Date of Patent: Apr. 21, 2020

(54) METHOD FOR INDUCING CEREBRAL CORTEX NEURONS

(71) Applicant: KYOTO UNIVERSITY, Kyoto (JP)

(72) Inventors: Jun Takahashi, Kyoto (JP); Makoto Motono, Kyoto (JP); Yoshihiko Ioroi, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 40 days.

(21) Appl. No.: 15/565,984

(22) PCT Filed: Apr. 14, 2016

(86) PCT No.: PCT/JP2016/062578
§ 371 (c)(1),
(2) Date: Oct. 12, 2017

(87) PCT Pub. No.: WO2016/167372
PCT Pub. Date: Oct. 20, 2016

(65) Prior Publication Data
US 2018/0094241 A1    Apr. 5, 2018

(30) Foreign Application Priority Data

Apr. 14, 2015 (JP) ................................. 2015-082497

(51) Int. Cl.
| C12N 5/00 | (2006.01) |
| C12N 5/0793 | (2010.01) |
| A61K 35/30 | (2015.01) |
| A61K 35/545 | (2015.01) |
| A61K 35/00 | (2006.01) |

(52) U.S. Cl.
CPC ............ *C12N 5/0619* (2013.01); *A61K 35/30* (2013.01); *A61K 35/00* (2013.01); *A61K 35/545* (2013.01); *C12N 2501/115* (2013.01); *C12N 2501/15* (2013.01); *C12N 2501/155* (2013.01); *C12N 2501/415* (2013.01); *C12N 2506/02* (2013.01); *C12N 2506/08* (2013.01); *C12N 2506/13* (2013.01); *C12N 2506/45* (2013.01)

(58) Field of Classification Search
CPC ......... C12N 5/0619; C12N 5/06; A61K 35/30
See application file for complete search history.

(56) References Cited

U.S. PATENT DOCUMENTS

2012/0190841 A1* 7/2012 Nemoto ............... A61K 31/585 540/115
2012/0276063 A1* 11/2012 Meyer .................. C12N 5/0619 424/93.7
2016/0243285 A1* 8/2016 Zhang ..................... A61L 27/52
2016/0311829 A1* 10/2016 Alam ................... C07D 487/04
2016/0312190 A1* 10/2016 Ghaedi ................. C12N 5/0688
2017/0247658 A1* 8/2017 Iseoka ..................... A61L 27/00
2019/0010451 A1* 1/2019 Zhang .................. C12N 5/0619

FOREIGN PATENT DOCUMENTS

| JP | 2015-19628 A | 2/2015 |
| WO | 2010/144696 A1 | 12/2010 |
| WO | 2014/176606 A1 | 10/2014 |

OTHER PUBLICATIONS

Kim JE, et al., Investigating synapse formation and function using human pluripotent stem cell-derived neurons, Proc Natl Acad Sci USA, 108: 3005-3010, 2011.
Hu BY, et al., Neural differentiation of human induced pluripotent stem cells follows developmental principles but with variable potency, Proc Natl Acad Sci USA, 107: 4335-4340, 2010.
Mariani J, et al., Modeling human cortical development in vitro using induced pluripotent stem cells, Proc Natl Acad Sci USA, 109: 12770-12775, 2012.
Tetsuhiro Kikuchi et al. , "Fuyu Baiyoho ni yoru Hito iPS Saibo kara no Shinkei Bunka Yudo", Annual Meeting of the Japan Neurosurgical Society Abstract, 2009, vol. 68th, 1Q-DP030-01.
Yu Kamishibahara, et al., Promotion of mouse embryonic stem cell differentiation by Rho kinase inhibitor Y-27632, Neuroscience Letters, 2014, vol. 579, p. 58-63.
English machine translation of Tetsuhiro Kikuchi et al. (IDS NPL No. 4) (2 pages).
English machine translation of Japanese Publication No. JP2015-19628, dated Feb. 2, 2015 (20 pages).
International Search Report for International Application No. PCT/JP2016/062578, dated Jul. 26, 2016 (2 pages).

* cited by examiner

*Primary Examiner* — Marcia S Noble
(74) *Attorney, Agent, or Firm* — Lucas & Mercanti, LLP

(57) ABSTRACT

Provided is a method for producing cerebral cortex neurons from pluripotent stem cells.

Provided is a method for producing cerebral cortex neurons from pluripotent stem cells, comprising (i) a step of performing a suspension culture of pluripotent stem cells in a culture medium containing a TGFβ inhibitor, bFGF, a Wnt inhibitor, and a BMP inhibitor, (ii) a step of performing a suspension culture of the cells obtained in the step (i) in a culture medium containing a Wnt inhibitor and a BMP inhibitor, and (iii) a step of further culturing the cells obtained in the step (ii).

12 Claims, 14 Drawing Sheets
(11 of 14 Drawing Sheet(s) Filed in Color)

Fig. 3
A
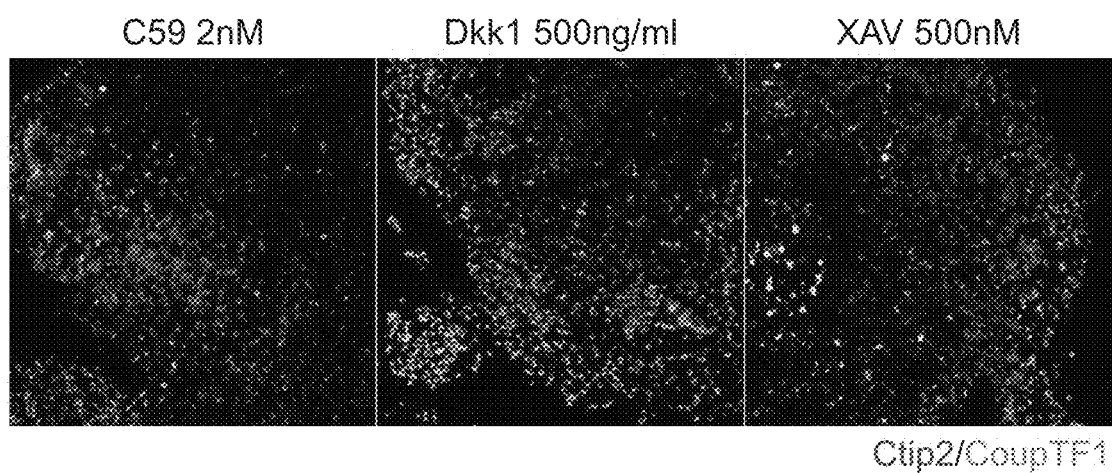
B
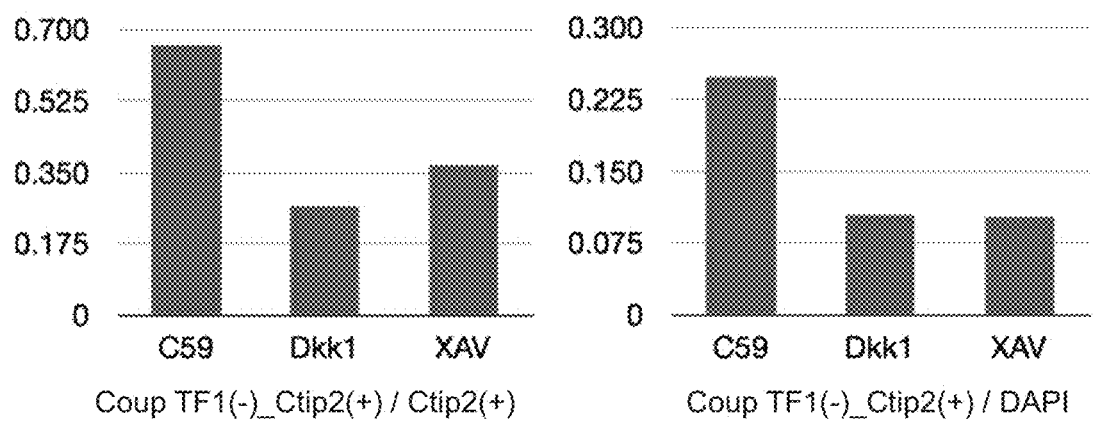

Fig. 4
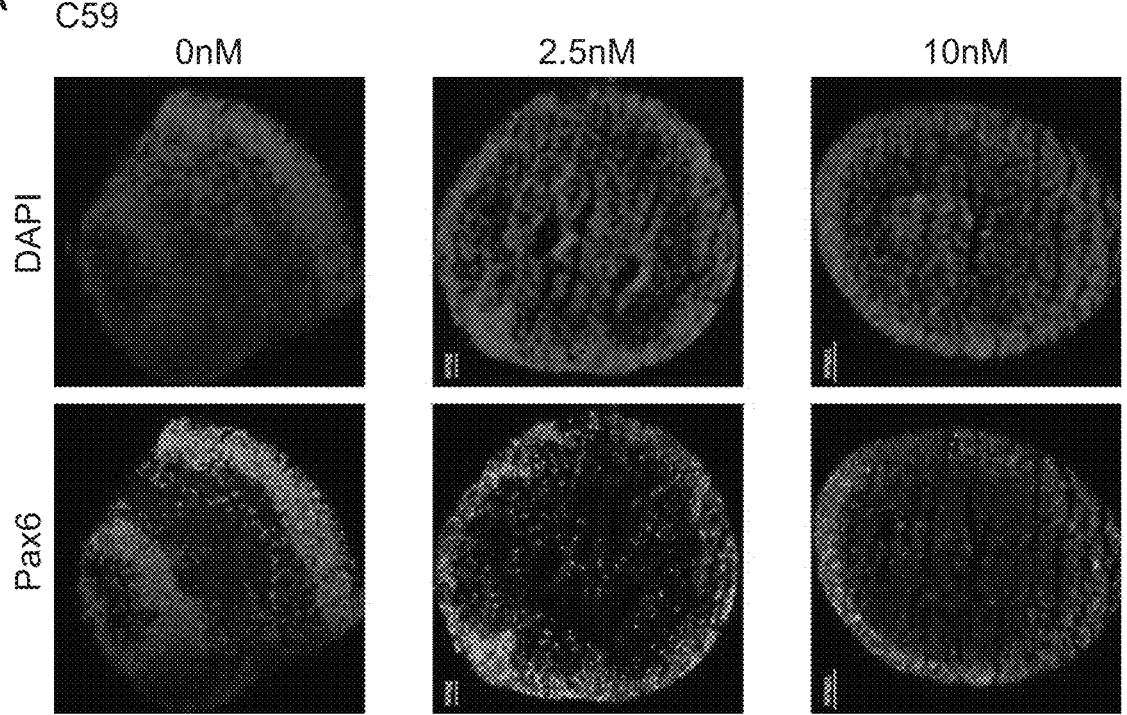
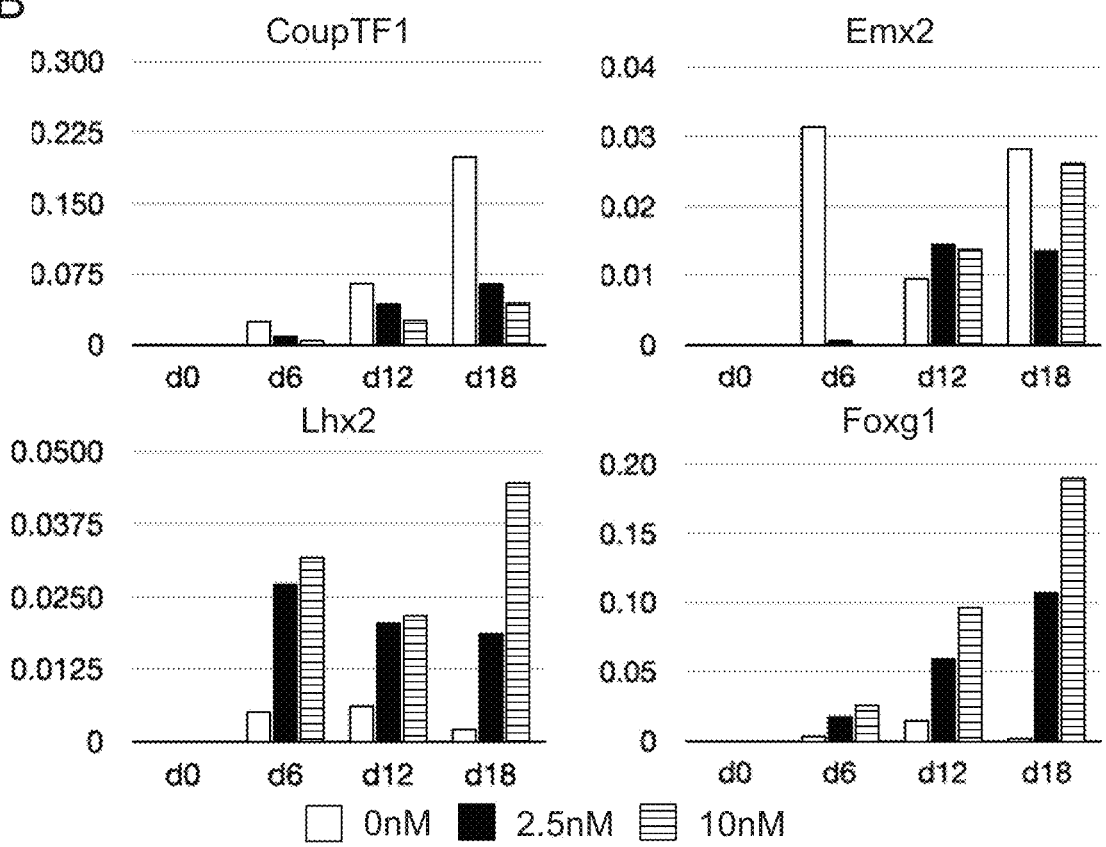

Fig. 5
A
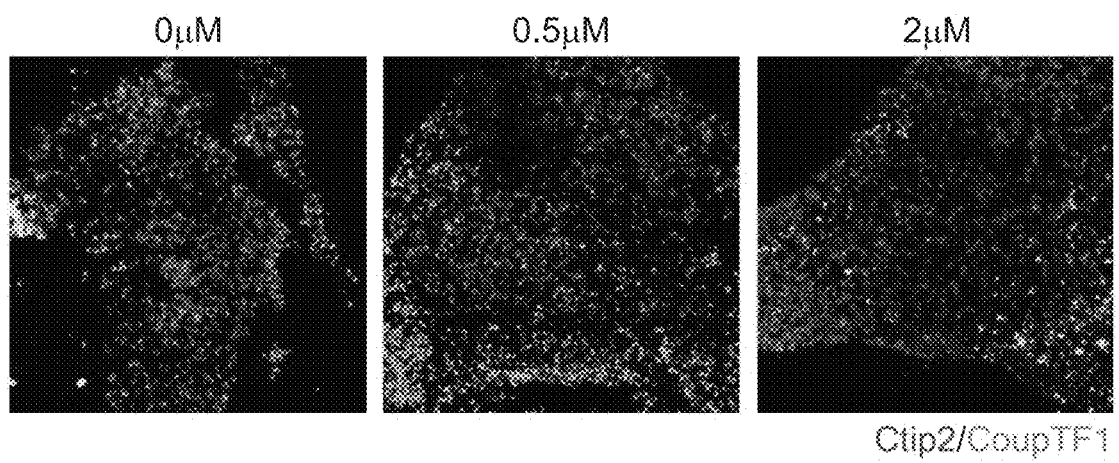
B
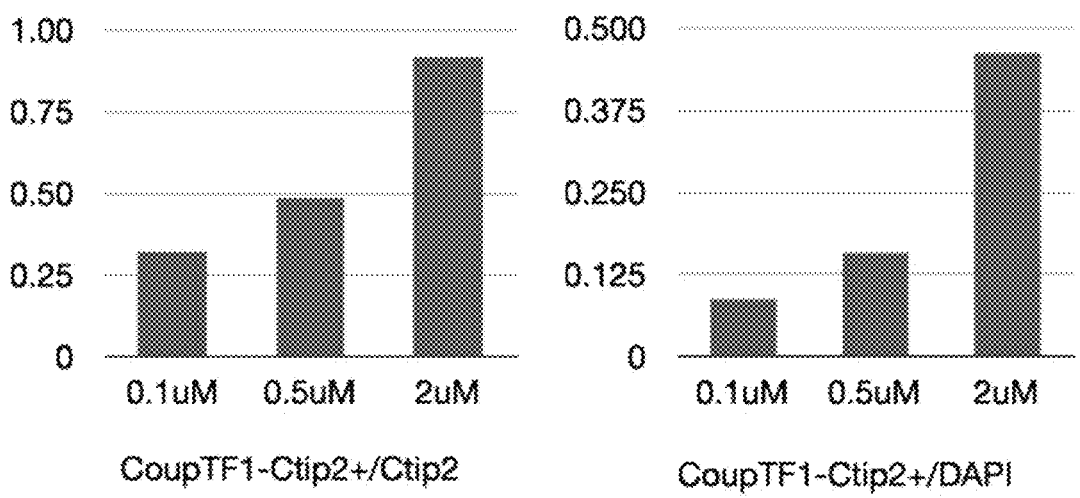
C
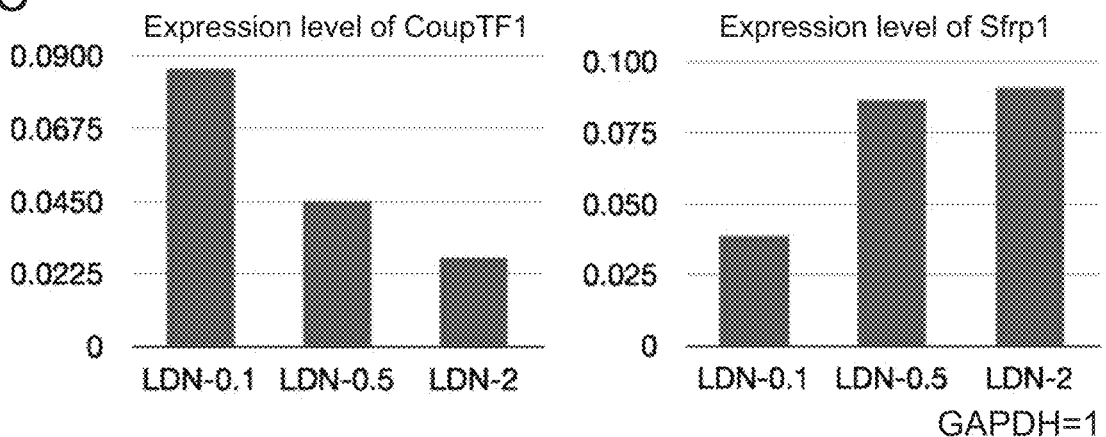

Fig. 6
A
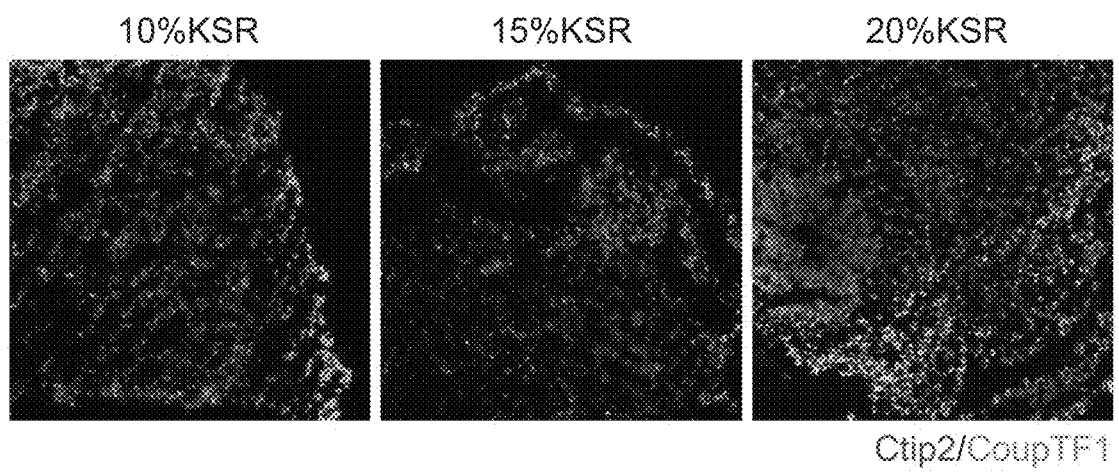
B
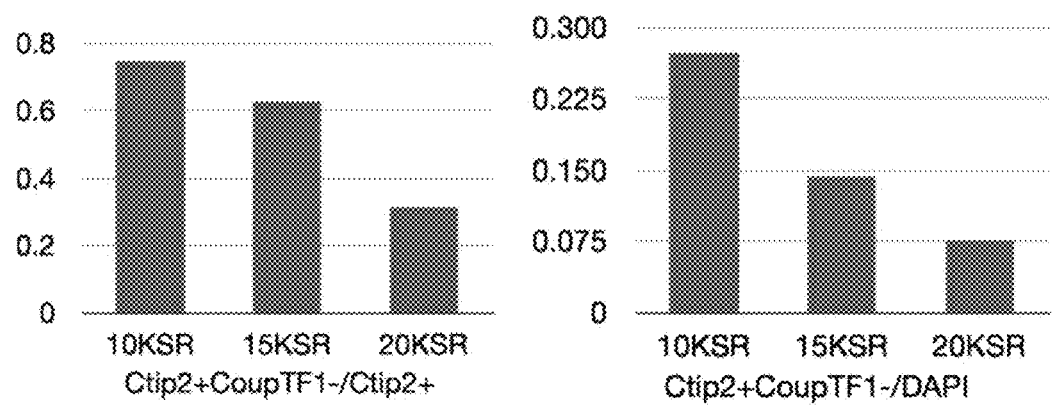
C
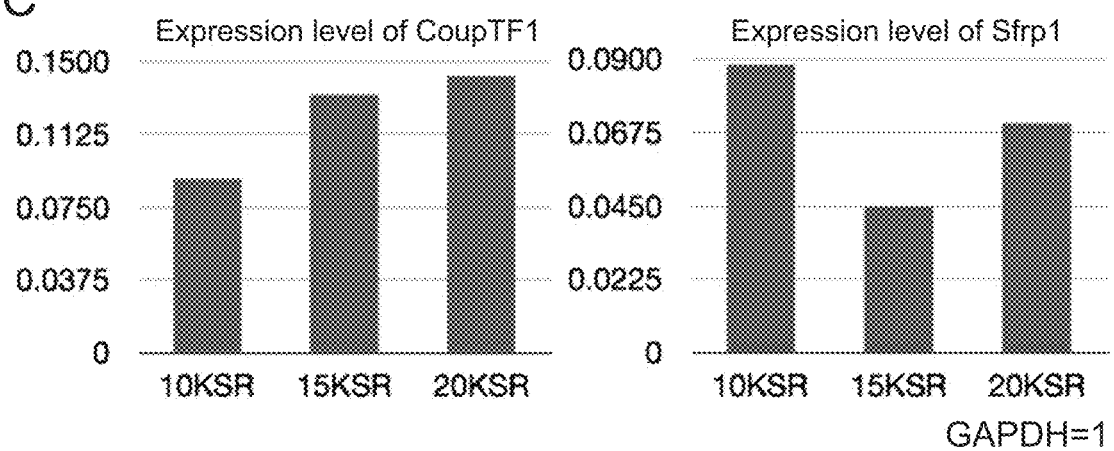

Fig. 7
A
A-83-01
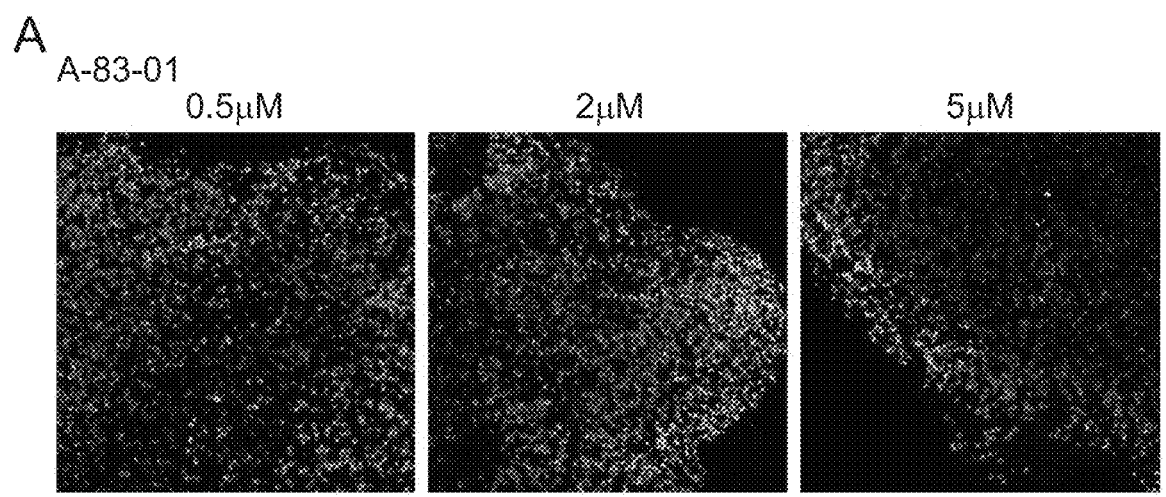
B
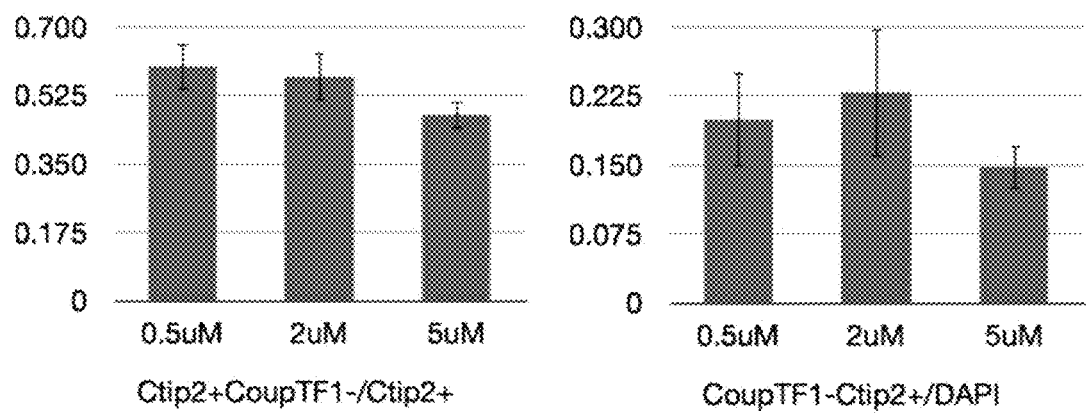

Fig. 10
A
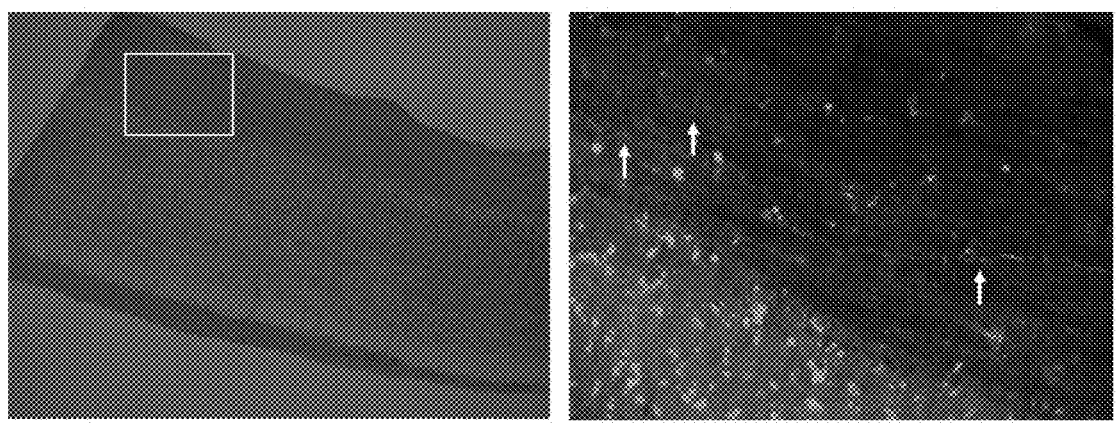
B
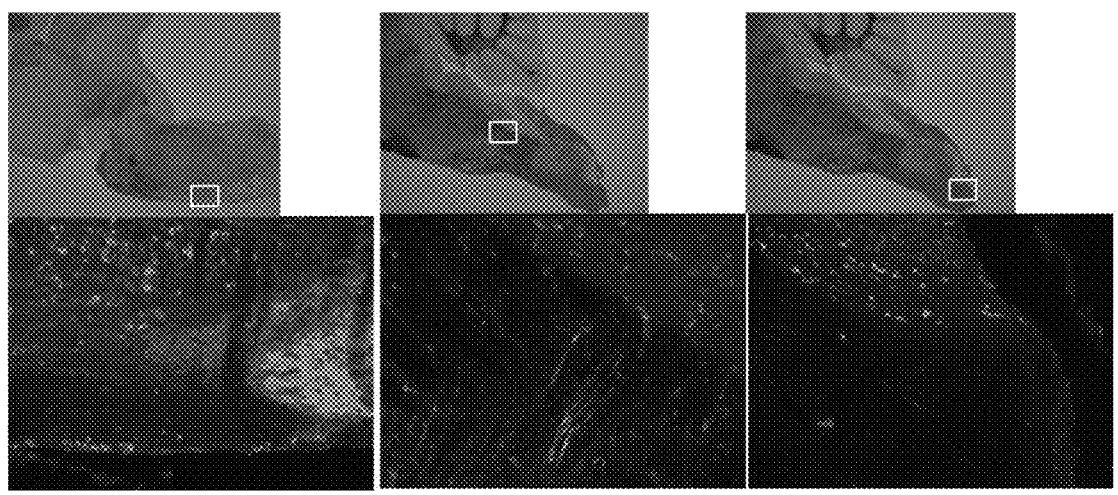

Day 48

Fig. 12
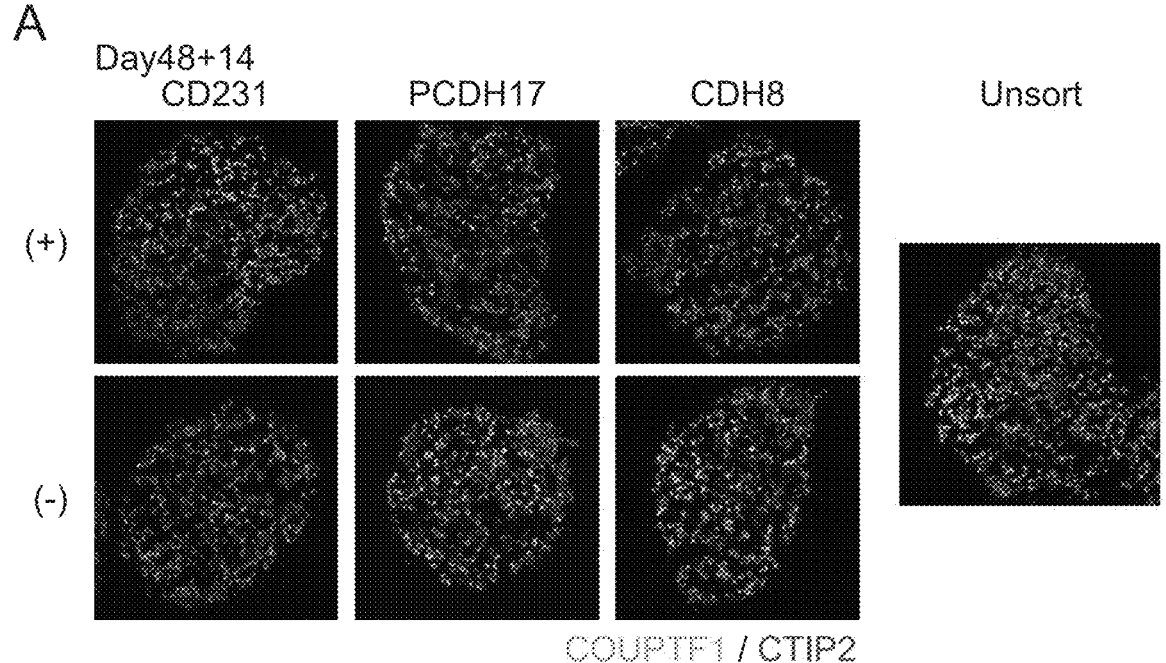
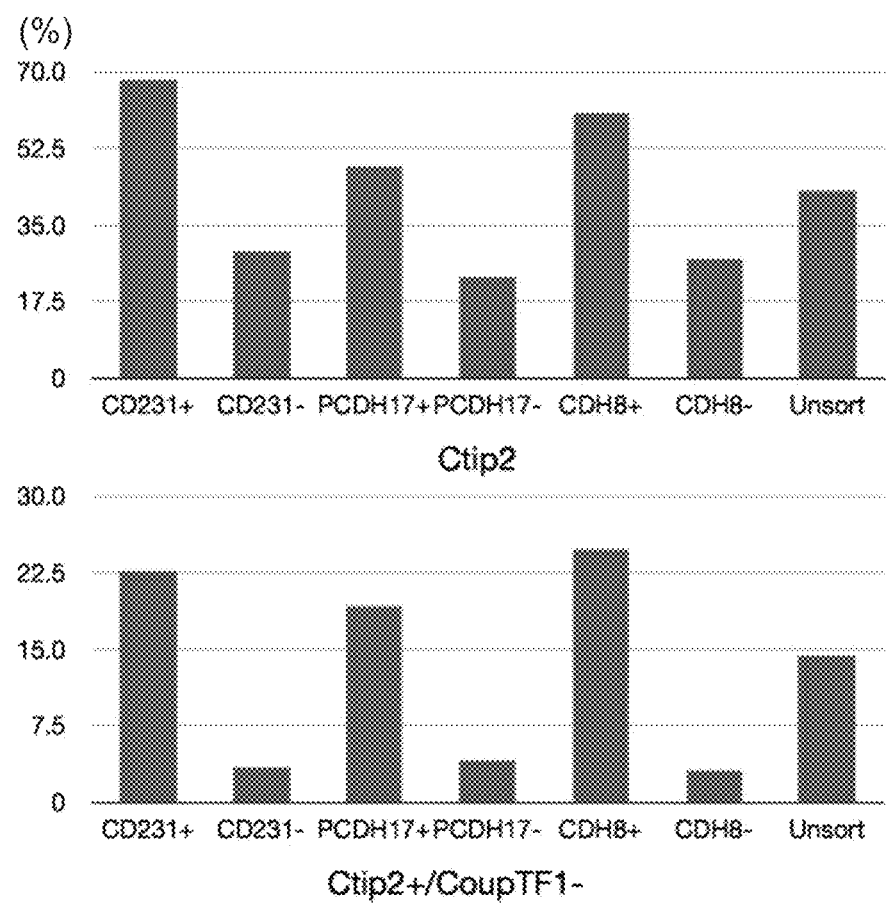

Fig. 13
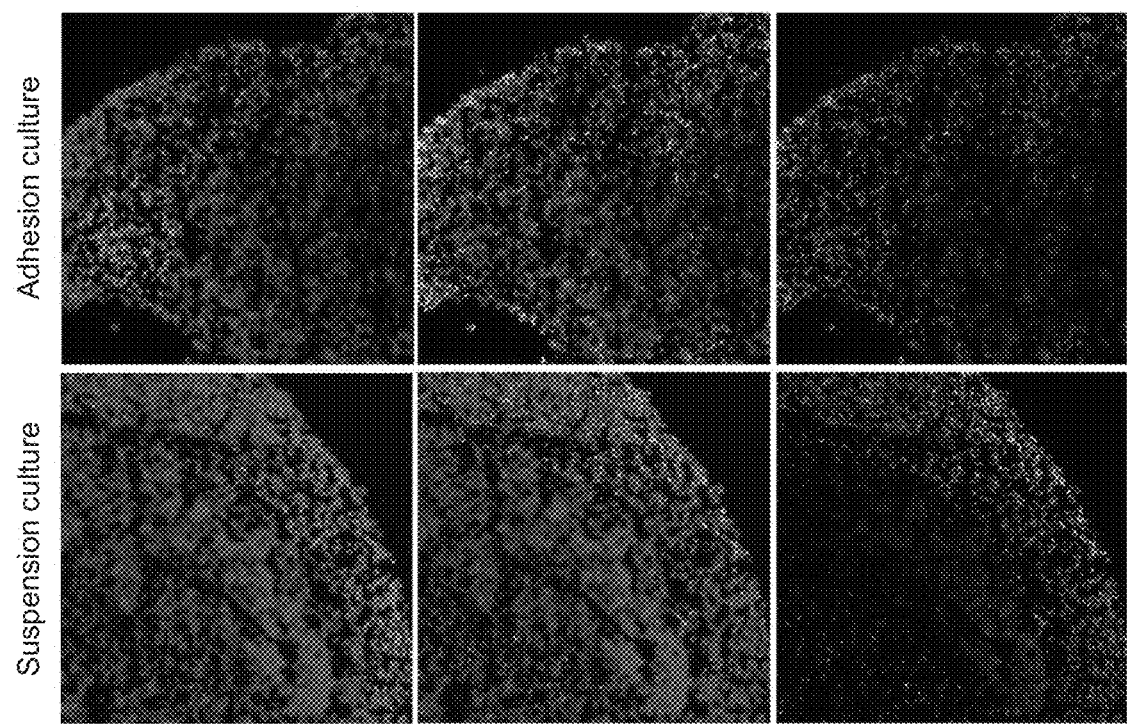
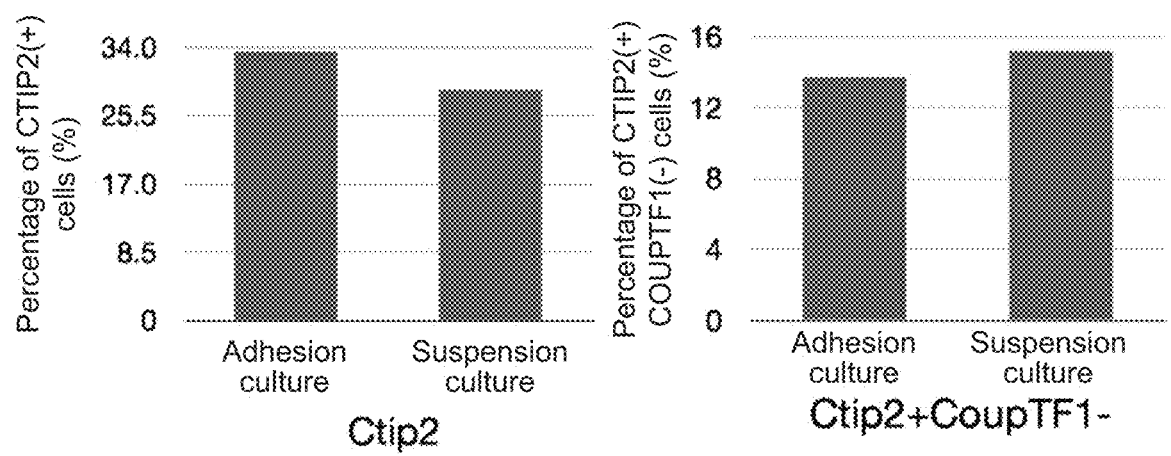

Fig. 14
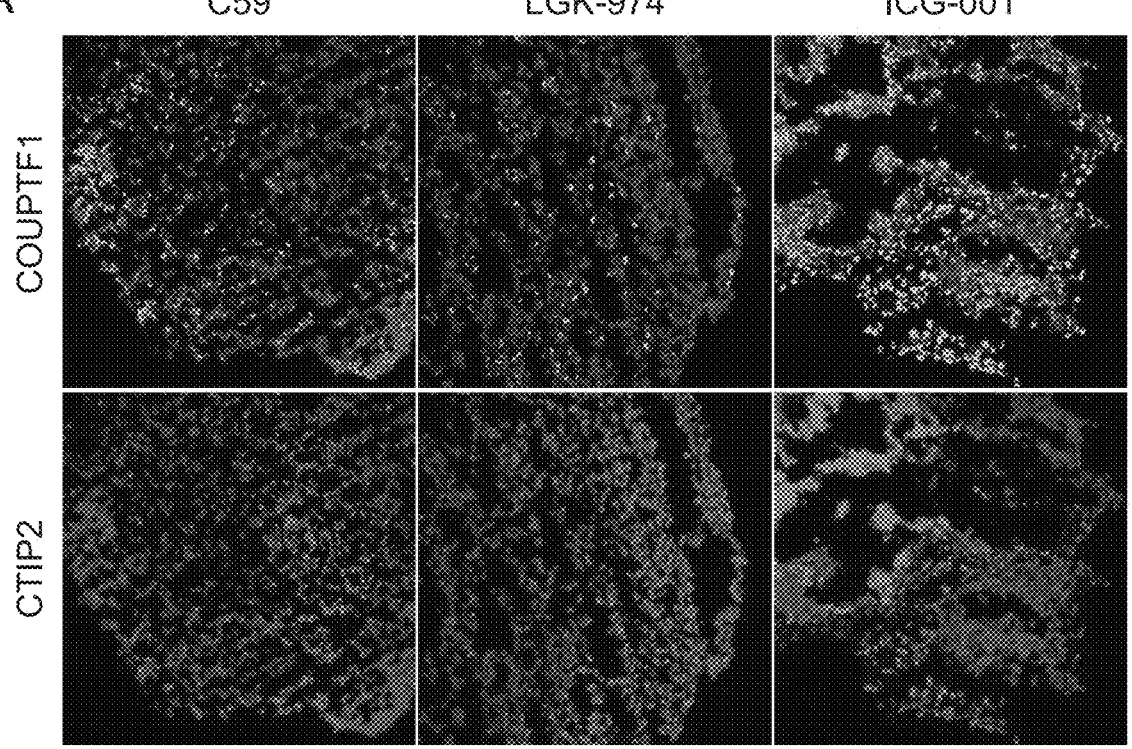
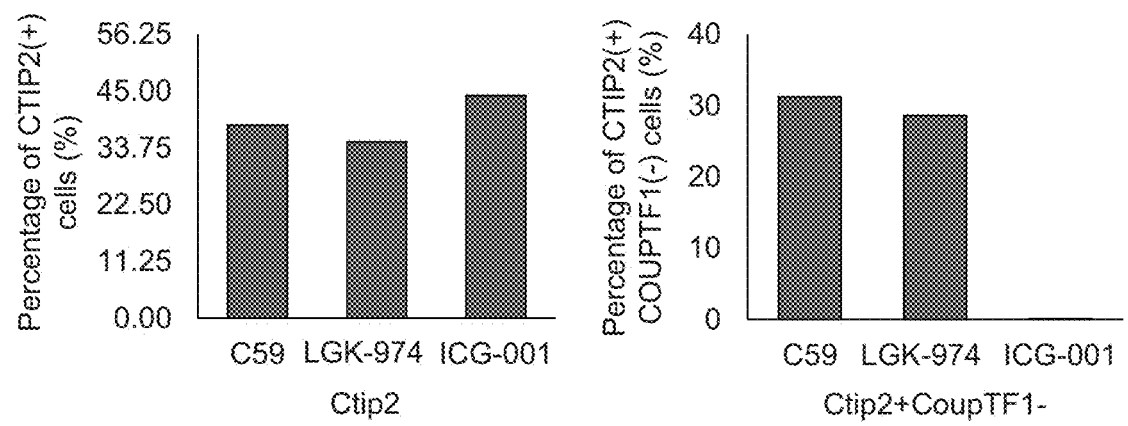

METHOD FOR INDUCING CEREBRAL CORTEX NEURONS

CROSS-REFERENCE TO RELATED APPLICATIONS

This application is a 371 of PCT/JP2016/062578, filed Apr. 14, 2016, which claims the benefit of Japanese Patent Application No. 2015-082497, filed Apr. 14, 2015.

TECHNICAL FIELD

The present invention relates to a method for producing cerebral cortex neurons.

BACKGROUND ART

Cerebral infarction, in which the necrosis of cerebral tissues and the like are caused by ischemia, is a high-frequency disease that is a principal cause of death. In addition, since this disease would leave aftereffects, many patients need care. Thus, cerebral infarction is a disease having serious problems even in terms of welfare. In recent years, it has been elucidated that neural stem cells are induced after the occurrence of cerebral infarction, and that the injured tissues are healed by the self-healing system of the tissues. However, if a large infarct area is developed, such self-healing does not occur. Hence, a transplantation treatment of administering exogenous nerve cells into the infarct area has been studied.

In recent years, a method of inducing pluripotent stem cells to various tissue cells has been developed, and there have been many reports regarding nerve cells (Non Patent Literatures 1, 2, and 3).

However, there is a room for improving an induction method for efficiently producing nerve cells suitable for regeneration of tissues after the development of cerebral infarction.

CITATION LIST

Non Patent Literature

Non Patent Literature 1 Kim J E, et al. Proc Natl Acad Sci USA 108: 3005-3010, 2011
Non Patent Literature 2 Hu B Y, et al. Proc Natl Acad Sci USA 107: 4335-4340, 2010
Non Patent Literature 3 Mariani J, et al. Proc Natl Acad Sci U.S.A. 109: 12770-12775, 2012

SUMMARY OF INVENTION

It is an object of the present invention to efficiently produce cerebral cortex neurons from pluripotent stem cells. Accordingly, it is the object of the present invention to provide a process of producing cerebral cortex neurons from pluripotent stem cells, or a kit necessary for the production.

The present inventors have conducted intensive studies directed towards achieving the aforementioned object, and as a result, the inventors have found that culture conditions are considered, as appropriate, in a step of inducing cerebral cortex neurons from pluripotent stem cells, and the obtained cerebral cortex neurons are then transplanted into the brain to extend axons, so as to make them compatible with the brain tissues, thereby completing the present invention.

The present invention is as follows.
[1] A method for producing cerebral cortex neurons from pluripotent stem cells, comprising the following steps:
(i) a step of performing a suspension culture of pluripotent stem cells in a culture medium containing a TGFβ inhibitor, bFGF, a Wnt inhibitor, and a BMP inhibitor,
(ii) a step of performing a suspension culture of the cells obtained in the step (i) in a culture medium containing a Wnt inhibitor and a BMP inhibitor, and
(iii) a step of culturing the cells obtained in the step (ii).
[2] The method according to the above [1], wherein the pluripotent stem cells are human pluripotent stem cells.
[3] The method according to the above [2], wherein the human pluripotent stem cells are human iPS cells or human ES cells.
[4] The method according to any one of the above [1] to [3], wherein the TGFβ inhibitor is SB431542 or A-83-01.
[5] The method according to any one of the above [1] to [4], wherein the Wnt inhibitor is a PORCN inhibitor.
[6] The method according to any one of the above [1] to [5], wherein the Wnt inhibitor is C59 or LGK-974.
[7] The method according to any one of the above [1] to [6], wherein the BMP inhibitor is LDN193189.
[8] The method according to any one of the above [1] to [7], wherein the culture medium further contains serum or a serum replacement.
[9] The method according to any one of the above [1] to [8], wherein the culture medium of the step (i) further contains a ROCK inhibitor.
[10] The method according to any one of the above [1] to [9], which further comprises (iv) a step of extracting from the cultured cells, the cells which are positive to at least one marker protein selected from the group consisting of CD231, PCDH17 and CDH8, after completion of the step (iii).
[11] The method according to any one of the above [1] to [10], wherein the cerebral cortex neurons are nerve cells in the corticocerebral motor area, which are positive to Ctip2 and negative to CoupTF1.
[12] The method according to any one of the above [1] to [11], wherein the step (i) is carried out for at least 3 days.
[13] The method according to any one of the above [1] to [12], wherein the step (ii) is carried out for at least 6 days.
[14] A cell culture comprising cerebral cortex neurons obtained by the method according to any one of the above [1] to [13].
[15] A kit for producing cerebral cortex neurons from pluripotent stem cells, comprising a TGFβ inhibitor, bFGF, a Wnt inhibitor, and a BMP inhibitor.
[16] The kit according to the above [15], wherein the TGFβ inhibitor is SB431542 or A-83-01, the Wnt inhibitor is C59 or LGK-974, and the BMP inhibitor is LDN193189.

According to the present invention, cerebral cortex neurons suitable for transplantation, which are useful for the treatment of cerebral infarction, etc., can be efficiently obtained.

The present description includes the contents as disclosed in Japanese Patent Application No. 2015-082497, which is a priority document of the present application.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 3A shows the stained images of cells on day 46 of the culture using C59, DKK1 or XAV as a Wnt inhibitor, with respect to Ctip2 (red) and CoupTF1 (green).

FIG. 3B includes graphs showing the content rate of CoupTF1-negative cells in Ctip2-positive cells after the culture for 46 days using C59, DKK1 or XAV as a Wnt inhibitor (left view), and the content rate of Ctip2-positive CoupTF1-negative cells in all cells (DAPI) (right view).

FIG. 4A shows the stained images of cells on day 18 of the culture using 0 nM, 2.5 nM or 10 nM C59 as a Wnt inhibitor, with respect to DAPI and Pax6. FIG. 4B includes graphs showing the expression levels of CoupTF1, Emx2, Lhx2 and Foxg1 in cells cultured using 0 nM, 2.5 nM or 10 nM C59 as a Wnt inhibitor, on the 0th day (d0), 6th day (d6), 12th day (d12) and 18th day (d18) of the culture.

FIG. 5A shows the stained images of cells on day 46 of the culture using 0.1 µM, 0.5 µM or 2 µM LDN193189, with respect to Ctip2 (red) and CoupTF1 (green).

FIG. 5B includes graphs showing the content rate of CoupTF1-negative cells in Ctip2-positive cells on day 46 of the culture using 0.1 µM, 0.5 µM or 2 µM LDN193189 (left view), and the content rate of Ctip2-positive CoupTF1-negative cells in all cells (DAPI) (right view). FIG. 5C includes graphs showing the expression levels of CoupTF1 and Sfrp1 in cells on day 46 of the culture using 0.1 µM, 0.5 µM or 2 µM LDN193189.

FIG. 6A shows the stained images of cells on day 46 of the culture using 10%, 15% or 20% KSR, with respect to Ctip2 (red) and CoupTF1 (green). FIG. 6B includes graphs showing the content rate of CoupTF1-negative cells in Ctip2-positive cells on day 46 of the culture using 10%, 15% or 20% KSR (left view), and the content rate of Ctip2-positive CoupTF1-negative cells in all cells (right view). FIG. 6C includes graphs showing the expression levels of CoupTF1 and Sfrp1 in cells on day 46 of the culture using 10%, 15% or 20% KSR.

FIG. 7A shows the stained images of cells on day 46 of the culture using 0.5 µM, 2 µM or 5 µM A-83-01, instead of using SB431542, with respect to Ctip2 (red) and CoupTF1 (green). FIG. 7B includes graphs showing the content rate of CoupTF1-negative cells in Ctip2-positive cells on day 46 of the culture using 0.5 µM, 2 µM or 5 µM A-83-01, instead of using SB431542 (left view), and the content rate of Ctip2-positive CoupTF1-negative cells in all cells (right view).

FIG. 10A shows a phase contrast image around the spinal cord, which is obtained 6 months after transplantation of the cells induced by the method of the present invention into the mouse motor area (left view), and an immune tissue image to human NCAM (right view). FIG. 10B shows phase contrast images in individual sites around the medulla oblongata, which are obtained 6 months after transplantation of the cells induced by the method of the present invention into the mouse motor area (upper views), and immune tissue images to human NCAM (lower views). The immunostained image surrounded with the frame in the phase contrast image is shown in each lower view.

FIG. 12A shows the stained images of the cells obtained by isolating each marker-positive cells (CD231, PCDH17 or CDH8) from the cells on day 48 of differentiation induction, and further culturing the isolated cells for 14 days, with respect to Ctip2 (red) and CoupTF1 (green). In the figure, the term "Unsort" indicates the cells obtained by separating the cells on day 48 of differentiation induction and further culturing the cells for 14 days. FIG. 12B includes graphs showing the content rate of Ctip2-positive cells on day 14 after the re-culture of each marker-positive cells (CD231, PCDH17 or CDH8) (shown with the symbol+in the figure) or each marker-negative cells (shown with the symbol−in the figure) (upper view), and the content rate of Ctip2-positive CoupTF1-negative cells (lower view). In the graph, the term "Unsort" indicates each content rate in the cells obtained by dissociating the cells on day 48 of differentiation induction and further culturing the cells for 14 days.

FIG. 13A shows the stained images of the cells on day 46 of differentiation induction by adhesion culture (upper case) or suspension culture (lower case), with respect to DAPI (blue)/Ctip2 (red) (left view), DAPI (blue)/CoupTF1 (green) (central view) and Ctip2 (red) and CoupTF1 (green) (right view). FIG. 13B includes graphs showing the content rate of Ctip2-positive cells on day 46 of differentiation induction by adhesion culture (Attach) or suspension culture (Floating) (left view), and the content rate of Ctip2-positive CoupTF1-negative cells (right view).

FIG. 14A shows the stained images of the cells on day 46 of the culture using C59, LGK-974 or ICG-001 as a WNT inhibitor, with respect to DAPI (blue), Ctip2 (red) and CoupTF1 (green). FIG. 14B includes graphs showing the content rate of Ctip2-positive cells in all cells (DAPI), after the cells have been cultured for 46 days using C59, LGK-974 or ICG-001 as a WNT inhibitor (left view), and the content rate of Ctip2-positive CoupTF1-negative cells in all cells (DAPI) (right view).

DESCRIPTION OF EMBODIMENTS

Figure 1:
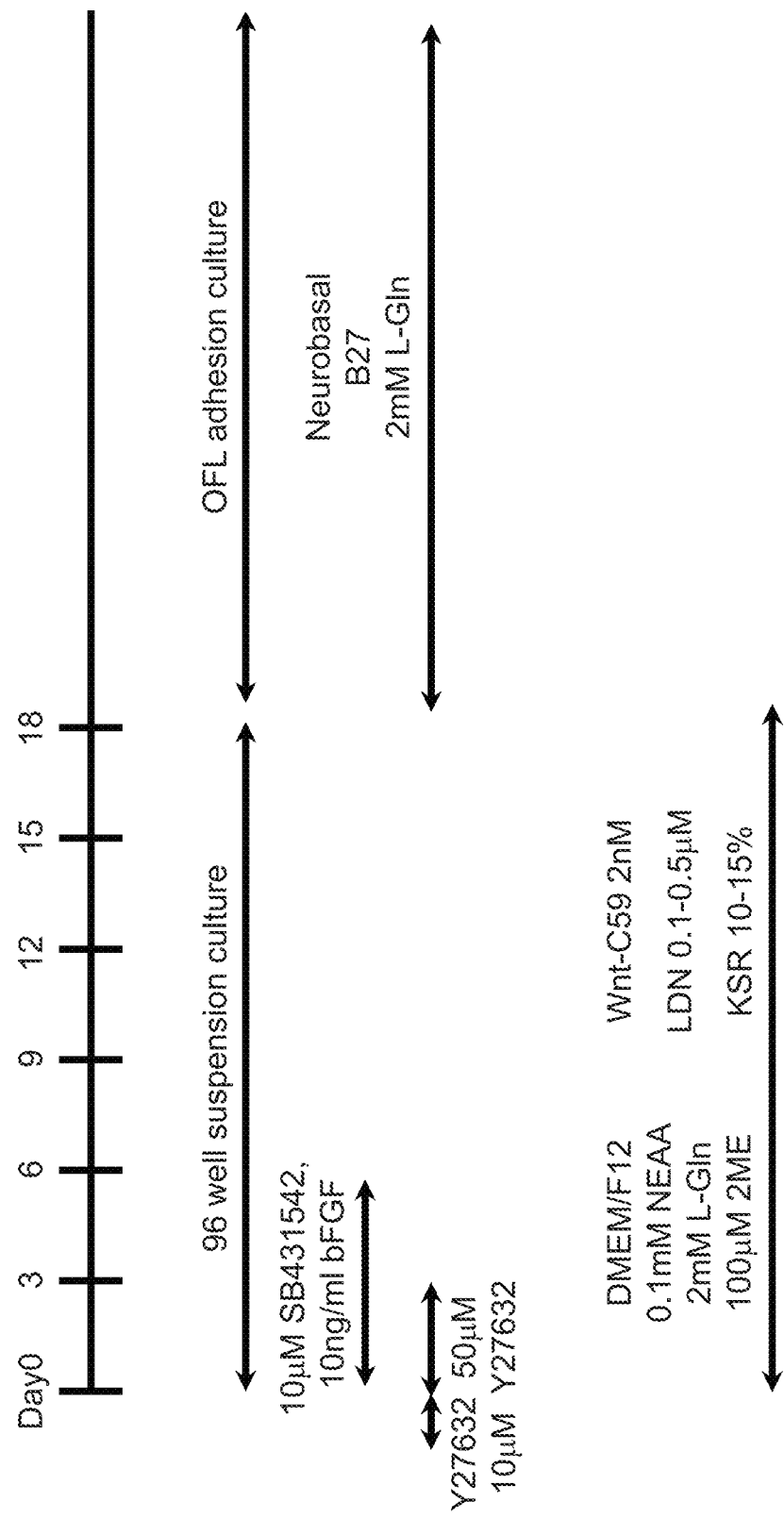
FIG. 1 shows an example of the production protocols of cerebral cortex neurons.

The present invention relates to a method for producing cerebral cortex neurons from pluripotent stem cells, comprising the following steps:

(i) a step of performing a suspension culture of pluripotent stem cells in a culture medium containing a TGFβ inhibitor, bFGF, a Wnt inhibitor, and a BMP inhibitor,
(ii) a step of performing a suspension culture of the cells obtained in the step (i) in a culture medium containing a Wnt inhibitor and a BMP inhibitor, and
(iii) a step of further culturing the cells obtained in the step (ii).

<Pluripotent Stem Cells>

The pluripotent stem cells that can be used in the present invention are stem cells having pluripotency for which the cells can differentiate into all cells existing in a living body, and also having proliferative ability. Specific examples of such pluripotent stem cells include, but are not limited to, embryonic stem (ES) cells, embryonic stem cells derived from a clone embryo obtained by cell nucleus transplantation (ntES), spermatogonial stem cells ("GS cells"), embryonic germ cells ("EG cells"), and induced pluripotent stem (iPS) cells. Preferred pluripotent stem cells are ES cells, ntES cells, and iPS cells. More preferred pluripotent stem cells are human pluripotent stem cells, and are particularly preferably human ES cells and human iPS cells.

(A) Embryonic Stem Cells

ES cells are stem cells having pluripotency and proliferative ability that is based on self-replication, which are established from the inner cell mass of the initial embryo (e.g., blastocyst) of mammals such as a human or a mouse.

The ES cells are stem cells from an embryo derived from the inner cell mass of a blastocyst that is an embryo at a 8-cell stage or at a morula stage of a fertilized egg, and the ES cells have an ability to differentiate into all types of cells constituting an adult body, what is called, differentiation pluripotency, and proliferative ability based on self-replication. The ES cells have been discovered from mice in 1981 (M. J. Evans and M. H. Kaufman (1981), Nature 292: 154-156), and thereafter, ES cell lines have been established also in primates such as humans or monkeys (J. A. Thomson et al. (1998), Science 282: 1145-1147, J. A. Thomson et al. (1995), Proc. Natl. Acad. Sci. USA, 92: 7844-7848, J. A. Thomson et al. (1996), Biol. Reprod., 55: 254-259 and J. A. Thomson and V. S. Marshall (1998), Curr. Top. Dev. Biol., 38: 133-165).

The ES cells can be established by extracting an inner cell mass from the blastocyst of the fertilized egg of a target animal, and then culturing the inner cell mass on fibroblasts as feeders. Moreover, the maintenance of ES cells by subculture can be carried out using a medium, to which substances such as a leukemia inhibitory factor (LIF) or a basic fibroblast growth factor (bFGF) have been added. Methods for establishing and maintaining human and monkey ES cells are described, for example, in H. Suemori et al. (2006), Biochem. Biophys. Res. Commun., 345: 926-932, M. Ueno et al. (2006), Proc. Natl. Acad. Sci. USA, 103: 9554-9559, H. Suemori et al. (2001), Dev. Dyn., 222: 273-279 and H. Kawasaki et al. (2002), Proc. Natl. Acad. Sci. USA, 99: 1580-1585, etc.

As a medium for production of ES cells, for example, a DMEM/F-12 medium supplemented with 0.1 mM 2-mercaptoethanol, 0.1 mM non-essential amino acid, 2 mM L-glutamic acid, 20% KSR and 4 ng/ml bFGF is used, and human ES cells can be maintained at 37° C. in 5% $CO_2$ under a humid atmosphere. Moreover, the ES cells need to be subcultured every 3 to 4 days, and the subculture can be carried out, for example, using 0.25% trypsin and 0.1 mg/ml collagenase IV in PBS (phosphate buffered saline) comprising 1 mM $CaCl_2$ and 20% KSR.

Selection of the ES cells can be generally carried out using, as an indicator, the expression of a gene marker such as alkaline phosphatase, Oct-3/4 or Nanog. In particular, selection of human ES cells can be carried out by detecting the expression of a gene marker such as OCT-3/4 or NANOG by a Real-Time PCR method, and/or by detecting a cell surface antigen such as SSEA-3, SSEA-4, TRA-1-60 or TRA-1-81 by an immunostaining method (Klimanskaya I, et al. (2006), Nature. 444: 481-485).

Human ES cell lines, for example, KhES-1, KhES-2 and KhES-3 are available from Institute for Frontier Medical Sciences, Kyoto University (Kyoto, Japan).

(B) Spermatogonial Stem Cells

Spermatogonial stem cells are pluripotent stem cells derived from the testis, which become an origin for spermatogenesis. These cells can be induced to differentiate into various types of cells, as in the case of the ES cells, and have such a property that, for example, a chimeric mouse can be produced by transplanting the cells into a mouse blastocyst (M. Kanatsu-Shinohara et al. (2003) Biol. Reprod., 69: 612-616; K. Shinohara et al. (2004), Cell, 119: 1001-1012). The spermatogonial stem cells are able to self-replicate in a medium comprising a glial cell line-derived neurotrophic factor (GDNF), and can also be obtained by repeatedly subculturing the cells under the culture conditions as those for the ES cells (Masanori TAKEBAYASHI et al. (2008), *Jikken Igaku*, Vol. 26, No. 5 (supplement), pp. 41 to 46, Yodosha Co., Ltd. (Tokyo, Japan)).

(C) Embryonic Germ Cells

Embryonic germ cells are cells having pluripotency similar to that of ES cells, which are established from primordial germ cells at the embryonic stage. The embryonic germ cells can be established by culturing primordial germ cells in the presence of substances such as LIF, bFGF, or a stem cell factor (Y. Matsui et al. (1992), Cell, 70: 841-847; J. L. Resnick et al. (1992), Nature, 359: 550-551).

(D) Induced Pluripotent Stem Cells

Induced pluripotent stem (iPS) cells are somatic cell-derived artificial stem cells having properties almost equivalent to those of ES cells, such as differentiation pluripotency and proliferative ability based on self-replication, which can be produced by introducing one or more types of specific nuclear reprogramming substances in the form of DNA or a protein into somatic cells, or by increasing the expression level of the endogenous mRNA or protein of the reprogramming substance, using one or more types of specific drugs (K. Takahashi and S. Yamanaka (2006) Cell, 126: 663-676, K. Takahashi et al. (2007) Cell, 131: 861-872, J. Yu et al. (2007) Science, 318: 1917-1920, M. Nakagawa et al. (2008) Nat. Biotechnol., 26: 101-106, International Publication WO 2007/069666 and International Publication WO 2010/068955). The nuclear reprogramming substance may be a gene specifically expressed in ES cells, or a gene playing an important role in the maintenance of the undifferentiated state of ES cells, or a gene product thereof, and thus, the type of the nuclear reprogramming substance is not particularly limited. Examples of such a nuclear reprogramming substance include Oct3/4, Klf4, Klf1, Klf2, Klf5, Sox2, Sox1, Sox3, Sox15, Sox17, Sox18, c-Myc, L-Myc, N-Myc, TERT, SV40 Large T antigen, HPV16 E6, HPV16 E7, Bmil, Lin28, Lin28b, Nanog, Esrrb, Esrrg, and Glis1. Upon the establishment of iPS cells, these reprogramming substances may be used in combination. Such a combination can be a combination comprising at least one, two or three types of the above-described reprogramming substances, and preferably, a combination of three or four types of the above-described reprogramming substances.

The nucleotide sequence information of the mouse and human cDNAs of each of the above-described nuclear reprogramming substances, and the amino acid sequence information of proteins encoded by the cDNAs, can be obtained by accessing the accession number of GenBank (NCBI, USA) or EMBL (Germany) described in WO 2007/069666. Moreover, the mouse and human cDNA sequence information of L-Myc, Lin28, Lin28b, Esrrb, Esrrg and Glis1, and the amino acid sequence information thereof, can be obtained by accessing the NCBI accession numbers shown in Table 1. A person skilled in the art could prepare a desired nuclear reprogramming substance according to a common method, based on the cDNA sequence or amino acid sequence information.

TABLE 1

| Gene name | Mouse | Human |
|---|---|---|
| L-Myc | NM_008506 | NM_001033081 |
| Lin28 | NM_145833 | NM_024674 |
| Lin28b | NM_001031772 | NM_001004317 |
| Esrrb | NM_011934 | NM_004452 |
| Esrrg | NM_011935 | NM_001438 |
| Glis1 | NM_147221 | NM_147193 |

These nuclear reprogramming substances may be each introduced in the form of proteins into somatic cells according to means such as lipofection, binding to a cell membrane permeable protein, or microinjection. Otherwise, the nuclear reprogramming substances may also be each introduced in the form of DNA into somatic cells according to means such as the use of a vector such as a virus, a plasmid or an artificial chromosome, lipofection, the use of liposome, or microinjection. Examples of the virus vector include a retrovirus vector, a lentivirus vector (these vectors are described in Cell, 126, pp. 663-676, 2006; Cell, 131, pp. 861-872, 2007; Science, 318, pp. 1917-1920, 2007), an adenovirus vector (Science, 322, 945-949, 2008), an adeno-associated virus vector, and a sendai virus vector (Proc Jpn Acad Ser B Phys Biol Sci. 85, 348-62, 2009). In addition, examples of the artificial chromosome vector include human artificial chromosome (HAC), yeast artificial chromosome (YAC), and bacterial artificial chromosome (BAC and PAC). As such a plasmid, a plasmid for mammalian cells can be used (Science, 322: 949-953, 2008). The vector can comprise regulatory sequences such as a promoter, an enhancer, a ribosome binding sequence, a terminator, and a polyadenylation site or a polyadenylation signal, such that the nuclear reprogramming substance can be expressed in the cell. Examples of the promoter used herein include an EF1α promoter, a CAG promoter, an SRα promoter, an SV40 promoter, an LTR promoter, a CMV (cytomegalovirus) promoter, an RSV (Rous sarcoma virus) promoter, MoMuLV (Moloney murine leukemia virus) LTR, and an HSV-TK (herpes simplex virus thymidine kinase) promoter. Among these promoters, preferred examples include an EF1α promoter, a CAG promoter, MoMuLV LTR, a CMV promoter, and an SRα promoter. Moreover, as necessary, the vector can comprise selection marker sequences such as a drug resistance gene (e.g., a kanamycin resistance gene, an ampicillin resistance gene, or a puromycin resistance gene), a thymidine kinase gene, and a diphtheria toxin gene or a fragment thereof, and reporter gene sequences such as a green fluorescent protein (GFP), β-glucuronidase (GUS) or FLAG. Furthermore, after introduction of the above-described vector into somatic cells, in order to cleave a gene encoding the nuclear reprogramming substance, or in order to cleave both a promoter and a gene encoding the nuclear reprogramming substance that binds to the promoter, the vector may have LoxP sequences before and after them. In another preferred embodiment, there can be applied a method, which comprises incorporating an introduced gene into a chromosome using a transposon, then allowing transferase to act on the cells, using a plasmid vector or an adenovirus vector, and then completely removing the introduced gene from the chromosome. An example of the preferred transposon is piggyBac that is a transposon derived from lepidopterous insects (Kaji, K. et al., (2009), Nature, 458: 771-775, Woltjen et al., (2009), Nature, 458: 766-770, WO 2010/012077). In addition, in order for the introduced gene to be replicated and be present in the episome even if it is not incorporated into the chromosome, the vector may comprise sequences associated with the origins of lymphotrophic herpes virus, BK virus and bovine papillomavirus and the replications thereof. Examples of such a sequence include EBNA-1 and oriP, and Large T and SV40ori sequences (WO 2009/115295, WO 2009/157201 and WO 2009/149233). Moreover, in order to simultaneously introduce two or more types of nuclear reprogramming substances into cells, an expression vector capable of expressing a gene as a polycistronic mRNA may be used. In order to allow a gene to express as a polycistronic mRNA, sequences encoding the gene may be bound to each other by IRES or foot-and-mouth disease virus (FMDV) 2A coding region (Science, 322: 949-953, 2008, WO 2009/092042 and WO 2009/152529).

Upon nuclear reprogramming, in order to enhance the efficiency of inducing iPS cells, in addition to the above-described factors, the following factors can also be used, for example: histone deacetylase (HDAC) inhibitors [e.g., low molecular weight inhibitors such as valproic acid (VPA) (Nat. Biotechnol., 26(7): 795-797 (2008)), trichostatin A, sodium butyrate, MC 1293 or M344; nucleic acid expression inhibitors such as siRNA and shRNA to HDAC (e.g., HDAC1 siRNA Smartpool (registered trademark) (Millipore), HuSH 29mer shRNA Constructs against HDAC1 (OriGene)); etc.], DNA methyl transferase inhibitors (e.g., 5'-azacytidine) (Nat. Biotechnol., 26(7): 795-797 (2008)), G9a histone methyl transferase inhibitors [e.g., low molecular weight inhibitors such as BIX-01294 (Cell Stem Cell, 2: 525-528 (2008)), nucleic acid expression inhibitors such as siRNA and shRNA to G9a (e.g., G9a siRNA (human) (Santa Cruz Biotechnology)), etc.], L-channel calcium agonists (e.g., Bayk8644) (Cell Stem Cell, 3, 568-574 (2008)), p53 inhibitors (e.g., siRNA and shRNA to p53) (Cell Stem Cell, 3, 475-479 (2008)), Wnt signaling activators (e.g., soluble Wnt3a) (Cell Stem Cell, 3, 132-135 (2008)), growth factors such as LIF or bFGF, ALK5 inhibitors (e.g., SB431542) (Nat. Methods, 6: 805-8 (2009)), mitogen-activated protein kinase signaling inhibitors, glycogen synthase kinase-3 inhibitors (PloS Biology, 6(10), 2237-2247 (2008)), miRNAs such as miR-291-3p, miR-294 or miR-295 (R. L. Judson et al., Nat. Biotech., 27:459-461 (2009)), etc.

Examples of a drug, which is used in a method of increasing the expression level of the endogenous protein of a nuclear reprogramming substance using the drug, include 6-bromoindirubin-3'-oxime, indirubin-5-nitro-3'-oxime, valproic acid, 2-(3-(6-methylpyridin-2-yl)-1H-pyrazol-4-yl)-1,5-naphthyridine, 1-(4-methylphenyl)-2-(4,5,6,7-tetrahydro-2-imino-3(2H)-benzothiazolyl)ethanone HBr (pifithrin-alpha), prostaglandin J2, and prostaglandin E2 (WO 2010/068955).

Examples of a culture medium used in induction of iPS cells include: (1) 10% to 15% FBS-containing DMEM, DMEM/F12, or DME medium (wherein these media can further comprise, as appropriate, LIF, penicillin/streptomycin, puromycin, L-glutamine, non-essential amino acids, β-mercaptoethanol, etc.); and (2) bFGF- or SCF-containing medium for the culture of ES cells, such as a medium for the culture of mouse ES cells (e.g., TX-WES medium, THROMBO X) or a medium for the culture of primate ES cells (e.g., a medium for the culture of primate (human or monkey) ES cells (sales company: ReproCELL Inc., Kyoto, Japan), mTeSR-1).

As an example of the culture method, somatic cells are allowed to come into contact with a nuclear reprogramming substance (DNA, RNA or a protein), for example, at 37° C. in the presence of 5% $CO_2$ in 10% FBS-containing DMEM or DMEM/F12 medium, the obtained mixture is then cultured for approximately 4 to 7 days, and then, the cultured cells were seeded again on feeder cells (e.g., mitomycin C-treated STO cells, SNL cells, etc.), and thereafter, the cells are cultured on a bFGF-containing medium for the culture of primate ES cells from approximately 10 days after the contact of the somatic cells with the nuclear reprogramming substance, so that ES cell-like colonies can be generated approximately 30 to approximately 45 days, or more days after the aforementioned contact. Moreover, in order to enhance the efficiency of inducing iPS cells, the cells may be cultured under conditions involving a low oxygen concentration of 5% to 10%.

Alternatively, the above-described cells are cultured on feeder cells (e.g., mitomycin C-treated STO cells or SNL cells) in a 10% FBS-containing DMEM medium (wherein this medium can further comprise, as appropriate, LIF, penicillin/streptomycin, puromycin, L-glutamine, non-essential amino acids, b-mercaptoethanol, etc.), so that ES cell-like colonies can be formed approximately 25 to approximately 30 days, or more days after initiation of the culture.

During the above-described culture, the medium is exchanged with a fresh medium once a day, from the 2nd day after initiation of the culture. The number of somatic cells used in the nuclear reprogramming is not limited. It is in the range from approximately $5 \times 10^3$ to approximately $5 \times 10^6$ cells per culture dish (100 $cm^2$).

When DNA comprising a drug resistance gene is used as a marker gene, the cells are cultured in a medium comprising the corresponding drug (i.e., a selective medium), so that marker gene-expressing cells can be selected. On the other hand, when the marker gene is a fluorescent protein gene, marker gene-expressing cells can be detected by observing the cells under a fluorescence microscope. When the marker gene is a chemiluminescent enzyme gene, marker gene-expressing cells can be detected by adding a chemiluminescent substrate to the cells, and when the marker gene is a coloring enzyme gene, marker gene-expressing cells can be detected by adding a chromogenic substrate to the cells.

The "somatic cells" used in the present description may be any types of cells derived from mammals, other than germ cells (e.g., a human, a mouse, a monkey, a swine, and a rat). Examples of such somatic cells include keratinized epithelial cells (e.g., epidermal keratinocytes), mucosal epithelial cells (e.g., epithelial cells in the tongue surface layer), exocrine gland epithelial cells (e.g., mammary gland cells), hormone secreting cells (e.g., adrenal medullary cells), cells for metabolism and/or storage (e.g., hepatic cells), lumen epithelial cells constituting interface (e.g., type I pneumocytes), lumen epithelial cells in the inner chain tube (e.g., vascular endothelial cells), ciliated cells with transporting capacity (e.g., respiratory tract epithelial cells), extracellular matrix secreting cells (e.g., fibroblasts), contractile cells (e.g., smooth muscle cells), cells in blood and immune system (e.g., T lymphocytes), sensation-related cells (e.g., rod cells), autonomic nervous system neurons (e.g., cholinergic neurons), supporting cells for sense organs and peripheral neurons (e.g., satellite cells), central nerve system nerve cells and glial cells (e.g., astroglial cells), pigment cells (e.g., retinal pigment epithelial cells), and their progenitor cells (tissue progenitor cells). The degree of differentiation of cells, the age of an animal from which cells are collected, and the like are not particularly limited. Either undifferentiated progenitor cells (including somatic stem cells), or finally differentiated mature cells can be used as an origin of somatic cells used in the present invention. Herein, examples of the undifferentiated progenitor cells include tissue stem cells (somatic stem cells) such as neural stem cells, hematopoietic stem cells, mesenchymal stem cells, or dental pulp stem cells.

In the present invention, the type of a mammal, from which somatic cells are collected, is not particularly limited, and it is preferably a human.

(E) ES Cells Derived from Clone Embryo Obtained by Nuclear Transplantation ntES cells are ES cells derived from a clone embryo that is produced by a nuclear transplantation technique, and these cells have almost the same properties as those of fertilized egg-derived ES cells (T. Wakayama et al. (2001), Science, 292: 740-743; S. Wakayama et al. (2005), Biol. Reprod., 72: 932-936; J. Byrne et al. (2007), Nature, 450: 497-502). Specifically, ntES (nuclear transfer ES) cells are established from the inner cell mass of a blastocyst derived from a clone embryo obtained by replacing the nucleus of an unfertilized egg with the nucleus of a somatic cell. For production of ntES cells, a combination of the nuclear transplantation technique (J. B. Cibelli et al. (1998), Nat. Biotechnol., 16: 642-646) with the technique of producing ES cells (as described above) can be utilized (Kiyoka WAKAYAMA, et al., (2008), *Jikken Igaku*, Vol. 26, No. 5 (supplement), pp. 47 to 52). Upon the nuclear transplantation, the nucleus of a somatic cell is injected into the unfertilized egg of a mammal, from which the nucleus has been removed, and it is then cultured for several hours for reprogramming.

(F) Fusion Stem Cells

Fusion stem cells are produced by fusing somatic cells with an ovum or ES cells. The fusion stem cells are stem cells having pluripotency similar to that of the fused ES cells and also having genes specific to somatic cells (Tada M et al. Curr Biol. 11: 1553-8, 2001; Cowan C A et al. Science. 2005 Aug. 26; 309(5739): 1369-73).

<Cerebral Cortex Neurons>

In the present invention, the cerebral cortex neurons comprise one or more cells selected from the group consisting of cerebral cortex nerve cells, cerebral cortex neural stem cells, and cerebral cortex neural progenitor cells, unless otherwise specified. The cerebral cortex neurons produced by the method of the present invention are preferably Foxg1-positive cells. In the present invention, examples of the Foxg1 include a polynucleotide having NCBI Accession No. NM_005249, and a protein encoded thereby. The cerebral cortex neurons produced by the method of the present invention are more preferably nerve cells in the corticocerebral motor area or upper motor neurons, namely, nerve cells in the front portion of the cerebral cortex, and are further preferably nerve cells in phase V of the corticocerebral motor area. Such nerve cells are a cell population characterized in that Ctip2 is positive to the cells, and thus, it can also be said that these nerve cells are characterized in that CoupTF1 is negative to the cells. In the present invention, examples of Ctip2 include polynucleotides having NCBI Accession No. NM_001282237, NM_001282238, NM_022898 or NM_138576, and proteins encoded thereby.

The cerebral cortex neurons produced in the present invention may also be produced as a cell population comprising other cell species. For example, the cerebral cortex neurons may account for 15% or more, 20% or more, 30% or more, 40% or more, or 50% or more in the produced cell population. After the cerebral cortex neurons have been produced by the method of the present invention, the obtained neurons may be concentrated. The method of concentrating cerebral cortex neurons is, for example, a method which comprises labeling with an antibody, cells, to which at least one marker protein selected from the group consisting of CD231, PCDH17 and CDH8 shows positive, and then concentrating the labeled cells using a flow cytometer (FACS) or a magnetic cell separation device (MACS). As the aforementioned antibody, a commercially available antibody can be utilized, as appropriate. Accordingly, the method of the present invention may further comprise, as a step (iv), a step of extracting cells, to which at least one marker protein selected from the group consisting of CD231, PCDH17 and CDH8 shows positive, from the cells obtained in the step (iii). After completion of the extraction, the culture may be further continued. An example of the culture method after completion of the extraction can be a method of culturing the cells under the same conditions as those applied in the step (iii), but is not particularly limited thereto.

<TGFβ Inhibitor>

In the present invention, the TGFβ inhibitor is a substance that inhibits signal transduction from the binding of TGFβ with a receptor to SMAD, and examples of the TGFβ inhibitor include a substance inhibiting the binding of TGFβ to an ALK family as a receptor and a substance inhibiting the phosphorylation of SMAD by the ALK family. Specific examples of such a TGFβ inhibitor include Lefty-1 (as exemplified by NCBI Accession Nos. NM_010094 (mouse) and NM_020997 (human)), SB431542 and SB202190 (R. K. Lindemann et al., Mol. Cancer, 2003, 2: 20), SB505124 (GlaxoSmithKline), NPC30345, SD093, SD908, SD208 (Scios), LY2109761, LY364947, LY580276 (Lilly Research Laboratories), A-83-01 (WO 2009146408), and the derivatives thereof. The TGFβ inhibitor used in the present invention can preferably be SB431542 represented by the following Formula I, or A-83-01 represented by the following Formula II.

[Formula 1]

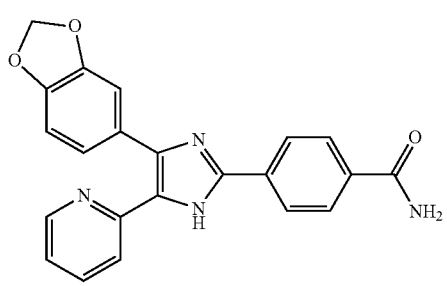

(Formula I)

[Formula 2]

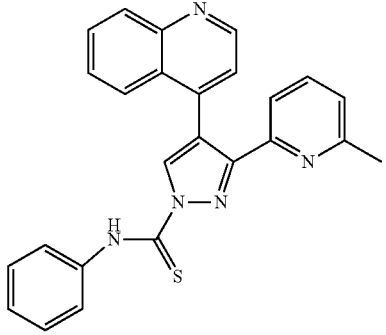

(Formula II)

The concentration of SB431542 in the culture medium is not particularly limited, as long as it is a concentration in which ALK5 is inhibited. Examples of the concentration of SB431542 include 100 nM, 500 nM, 750 nM, 1 μM, 2 μM, 3 μM, 4 μM, 5 μM, μM, 6 μM, 7 μM, 8 μM, 9 μM, 10 μM, 15 μM, 20 μM, 25 μM, 30 μM, 40 μM, 50 μM, 60 μM, 70 μM, 80 μM, 90 μM, 100 μM, 500 μM and 1 mM, but are not limited thereto. The concentration of SB431542 in the culture medium is preferably from 1 μM to 100 μM and is more preferably 10 μM.

The concentration of A-83-01 in the culture medium is not particularly limited, as long as it is a concentration in which ALK5 is inhibited. Examples of the concentration of A-83-01 include 1 nM, 10 nM, 50 nM, 100 nM, 500 nM, 750 nM, 1 μM, 2 μM, 3 μM, 4 μM, 5 μM, 6 μM, 7 μM, 8 μM, 9 μM, 10 μM, 15 μM, 20 μM, 25 μM, 30 μM, 40 μM, and 50 μM, but are not limited thereto. The concentration of A-83-01 in the culture medium is preferably from 500 nM to 5 μM, and is more preferably from 500 nM to 2

<bFGF>

In the present invention, bFGF is also referred to as FGF2. Since the bFGF is commercially available, for example, from Wako Pure Chemical Industries, Ltd., Invitrogen, etc., such commercially available products can be easily used. However, the bFGF may also be obtained by allowing cells to forcibly express the bFGF according to a method known to a person skilled in the art.

Examples of the concentration of bFGF in the culture medium include 0.1 ng/mL, 0.5 ng/mL, 1 ng/mL, 2 ng/mL, 3 ng/mL, 4 ng/mL, 5 ng/mL, 6 ng/mL, 7 ng/mL, 8 ng/mL, 9 ng/mL, 10 ng/mL, 20 ng/mL, 30 ng/mL, 40 ng/mL, 50 ng/mL, 60 ng/mL, 70 ng/mL, 80 ng/mL, 90 ng/mL, 100 ng/mL, 500 ng/mL, and 1000 ng/mL, but are not limited thereto. The concentration of bFGF in the culture medium is preferably from 1 ng/mL to 100 ng/mL, and is more preferably 10 ng/mL.

<Wnt Inhibitor>

In the present invention, the Wnt inhibitor is a substance that suppresses generation of Wnt, or a substance that inhibits signal transduction from the binding of Wnt with a receptor to accumulation of β catenin. Examples of the Wnt inhibitor include a substance inhibiting the binding of Wnt to a Frizzled family as a receptor and a substance promoting decomposition of β catenin. Specific examples of such a Wnt inhibitor include a DKK1 protein (e.g., in the case of a human, NCBI Accession No.: NM_012242), sclerostin (e.g., in the case of a human, NCBI Accession No.: NM_025237), IWR-1 (Merck Millipore), IWP-2 (Sigma-Aldrich), IWP-3 (Sigma-Aldrich), IWP-4 (Sigma-Aldrich), IWP-L6 (EMD Millipore), C59 (or Wnt-059) (Cellagen Technology), ICG-001 (Cellagen Technology), LGK-974 (or NVP-LGK-974)

(Cellagen Technology), FH535 (Sigma-Aldrich), WIKI4 (Sigma-Aldrich), KY02111 (Minami I, et al, Cell Rep. 2: 1448-1460, 2012), PNU-74654 (Sigma-Aldrich), XAV939 (Stemgent), and the derivatives thereof. Upon production of cerebral cortex neurons from pluripotent stem cells in the present invention, the preferred Wnt inhibitor is a substance suppressing generation of Wnt, and an example of such a substance can be a substance that inhibits PORCN associated with the processing of the Wnt protein (in the case of a human, proteins having NCBI Accession Nos. NP_001269096, NP_073736, NP_982299, NP_982300 and NP_982301 are exemplified). Specific examples include C59, IWP-3, IWP-4, IWP-L6 and LGK-974. In the present invention, a more preferred Wnt inhibitor is C59 represented by the following Formula III.

[Formula 3]

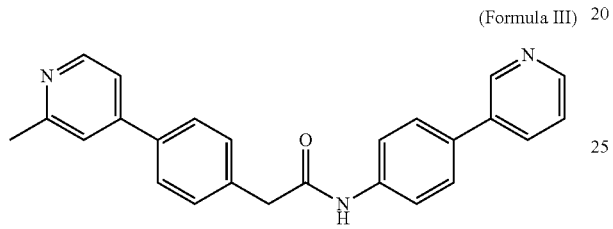

(Formula III)

The concentration of C59 in the culture medium is not particularly limited, as long as it is a concentration in which Wnt is inhibited. Examples of the concentration of C59 include 0.1 nM, 0.5 nM, 1 nM, 2 nM, 2.5 nM, 3 nM, 4 nM, 5 nM, 6 nM, 7 nM, 7.5 nM, 8 nM, 9 nM, 10 nM, 20 nM, 30 nM, 40 nM, 50 nM, 60 nM, 70 nM, 80 nM, 90 nM, and 100 nM, but are not limited thereto. The concentration of C59 in the culture medium is preferably from 1 nM to 50 nM, for example, from 2 nM to 50 nM, and it is more preferably from 10 nM to 50 nM. Otherwise, it is a concentration of less than 10 nM, and it is, for example, 2 nM or more and less than 10 nM.

Also, in the present invention, LGK-974 represented by the following Formula VI can preferably be used as a Wnt inhibitor.

(Formula VI)

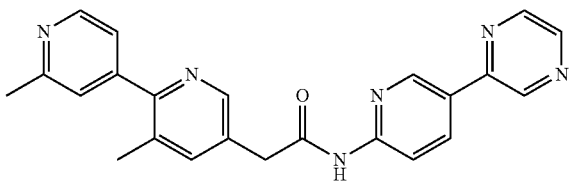

The concentration of LGK-974 in the culture medium is not particularly limited, as long as it is a concentration in which Wnt is inhibited. Examples of the concentration of LGK-974 include 1 nM, 10 nM, 25 nM, 50 nM, 100 nM, 150 nM, 200 nM, 500 nM, 750 nM, and 1 µM, but are not limited thereto. The concentration of LGK-974 in the culture medium is preferably from 1 nM to 1 µM, for example, from 1 nM to 500 nM, and it is more preferably from 10 nM to 200 nM. Otherwise, it is a concentration from 10 nM to 150 nM, and it is, for example, 10 nM or more and 100 nM or less.

<BMP Inhibitor>

In the present invention, examples of the BMP inhibitor include proteinaceous inhibitors such as Chordin, Noggin or Follistatin, Dorsomorphin (i.e., 6-[4-(2-piperidin-1-yl-ethoxy)phenyl]-3-pyridin-4-yl-pyrazolo[1,5-a]pyrimidine) or a derivative thereof (P. B. Yu et al. (2007), Circulation, 116: II_60; P. B. Yu et al. (2008), Nat. Chem. Biol., 4: 33-41; J. Hao et al. (2008), PLoS ONE, 3(8): e2904), and LDN193189 (i.e., 4-(6-(4-(piperazin-1-yl)phenyl)pyrazolo [1,5-a]pyrimidin-3-yl)quinoline). Dorsomorphin and LDN193189 are commercially available, and can be acquired from Sigma-Aldrich and Stemgent, respectively. The BMP inhibitor used in the present invention can preferably be LDN193189 represented by the following Formula IV.

[Formula 4]

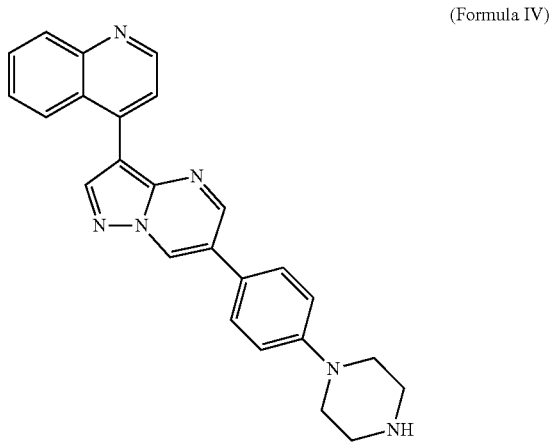

(Formula IV)

The concentration of LDN193189 in the culture medium is not particularly limited, as long as it is a concentration in which BMP is inhibited. Examples of the concentration of LDN193189 include 1 nM, 10 nM, 50 nM, 100 nM, 500 nM, 750 nM, 1 µM, 2 µM, 3 µM, 4 µM, 5 µM, 6 µM, 7 µM, 8 µM, 9 µM, 10 µM, 15 µM, 20 µM, 25 µM, 30 µM, 40 µM, and 50 µM, but are not limited thereto. The concentration of LDN193189 in the culture medium is preferably 2 µM or less, for example, from 100 nM to 2 µM, and it is more preferably from 500 nM to 2 µM. Otherwise, it is a concentration of less than 2 µM for example, 100 nM or more and less than 2 µM, and it is more preferably 500 nM or more and less than 2 µM.

<Step (i)>

The culture medium used in step (i) of the present invention can be prepared by adding the aforementioned TGFβ inhibitor, bFGF, Wnt inhibitor and BMP inhibitor to a medium for the culture of animal cells, which is used as a basal medium. Examples of the basal medium include Glasgow's Minimal Essential Medium (GMEM), IMDM medium, Medium 199, Eagle's Minimum Essential Medium (EMEM), αMEM medium, Dulbecco's modified Eagle's Medium (DMEM), Ham's F12 medium, RPMI 1640 medium, Fischer's medium, Neurobasal Medium (Invitrogen), and a mixed medium thereof. The basal medium is preferably a medium prepared by mixing DMEM and Ham's F12 medium at a mixing ratio of 1:1. The basal medium may comprise serum, or may comprise a serum replacement, instead of such serum. Examples of the serum replacement include albumin, transferrin, Knockout Serum Replacement (KSR) (a serum replacement for FBS used in the culture of ES cells), N2 supplement (Invitrogen), B27 supplement (Invitrogen), fatty acid, insulin, a collagen precursor, a trace element, and a combination of multiple substances selected from the aforementioned substances. The serum replacement is preferably KSR. When KSR is used in the step (i) of the present invention, examples of the concentration of the KSR in the basal medium include 5%, 10%, 11%, 12%, 13%, 14%, 15%, 16%, 17%, 18%, 19%, and 20%. The concentration of KSR is preferably less than 20%, for example, 10% or more and 15% or less. The basal medium can also comprise one or more substances selected from 2-mercaptoethanol, 3'-thiol glycerol, lipid, amino acid, L-glutamine, Glutamax (Invitrogen), non-essential amino acid, vitamin, a growth factor, a low molecular weight compound, an antibiotic, an antioxidant, pyruvic acid, a buffer, inorganic salts, and the like. The preferred basal medium is a medium prepared by mixing DMEM comprising KSR, 2-mercaptoethanol, non-essential amino acid and L-glutamine with Ham's F12 medium at a mixing ratio of 1:1.

In the step (i) of the present invention, pluripotent stem cells may be used after they have been dissociated. Examples of such a method of dissociating the cells include a method of mechanically dissociating the pluripotent stem cells, and a dissociation method of using a dissociation solution having protease activity and collagenase activity (e.g., Accutase (registered trademark), Accumax (registered trademark), etc.), or using a dissociation solution having only collagenase activity. Preferably, a method of dissociating pluripotent stem cells using a dissociation solution (e.g., Accumax) is applied. When the cells are dissociated, it is desired to add a ROCK inhibitor, as appropriate, after the dissociation of the cells, and then, to culture the obtained mixture. When such a ROCK inhibitor is added, the inhibitor may be added for at least 1 day, and may be then cultured. Alternatively, the pluripotent stem cells may also be cultured in a medium comprising such a ROCK inhibitor from one or more days before the dissociation of the cells, and preferably from one day before the dissociation of the cells.

In the present invention, the ROCK inhibitor is not particularly limited, as long as it is able to suppress the function of Rho kinase (ROCK). Examples of the ROCK inhibitor include Y-27632 (see, for example, Ishizaki et al., Mol. Pharmacol. 57, 976-983 (2000); Narumiya et al., Methods Enzymol. 325, 273-284 (2000)), Fasudil/HA1077 (see, for example, Uenata et al., Nature 389: 990-994 (1997)), H-1152 (see, for example, Sasaki et al., Pharmacol. Ther. 93: 225-232 (2002)), Wf-536 (see, for example, Nakajima et al., Cancer Chemother Pharmacol. 52(4): 319-324 (2003)), their derivatives, and also, an antisense nucleic acid, an RNA interference inducing nucleic acid (e.g., siRNA) and a dominant negative mutant, which react against ROCK, and their expression vectors. In addition, since other low molecular weight compounds have also been known as ROCK inhibitors, such compounds or their derivatives can also be used in the present invention (see, for example, U.S. Patent Application Laid-Open Nos. 20050209261, 20050192304, 20040014755, 20040002508, 20040002507, 20030125344 and 20030087919, and International Publication Nos. WO 2003/062227, WO 2003/059913, WO 2003/062225, WO 2002/076976 and WO 2004/039796). In the present invention, one or two or more types of ROCK inhibitors can be used. The ROCK inhibitor used in the present invention can preferably be Y-27632 represented by the following (V).

[Formula 5]

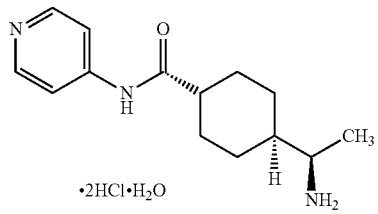

(Formula V)

Examples of the concentration of Y-27632 in the medium include 100 nM, 500 nM, 750 nM, 1 μM, 2 μM, 3 μM, 4 μM, 5 μM, 6 μM, 7 μM, 8 μM, 9 μM, 10 μM, 15 μM, 20 μM, 25 μM, 30 μM, 40 μM, 50 μM, 60 μM, 70 μM, 80 μM, 90 μM, and 100 μM, but are not limited thereto. The concentration of Y-27632 is preferably 10 μM or more and 50 μM or less.

The culture in the step (i) of the present invention is preferably carried out by a suspension culture. In the present invention, the suspension culture means that the cells are added into a culture vessel in a non-adhesion state to form an aggregate (which is also referred to as a "sphere") and the culture is then carried out, and thus, it is not particularly limited. It is a culture that is carried out, using a culture vessel that has not been artificially treated (e.g., a coating treatment using an extracellular matrix, etc.) for the purpose of improving the adhesiveness of the vessel with cells, or using a culture vessel that has been subjected to a coating treatment of artificially suppressing adhesion (e.g., polyhydroxyethyl methacrylate (poly-HEMA), nonionic surfactant polyol (Pluronic F-127, etc.), or a phospholipid-like structure (e.g., a water-soluble polymer (Lipidure) comprising, as a constituting unit, 2-methacryloyloxyethyl phosphorylcholine).

With regard to the culture conditions applied in the step (i) of the present invention, the culture temperature is not particularly limited, and it is approximately 30° C. to 40° C., and preferably approximately 37° C. The culture is carried out under a $CO_2$-containing air atmosphere, and the $CO_2$ concentration is preferably approximately 2% to 5%. The $O_2$ concentration may be an $O_2$ concentration in an ordinary air, or it may be either a higher oxygen condition than usual, or a lower oxygen condition than usual. In the present invention, examples of such a higher oxygen condition include an $O_2$ concentration of 25% or more, an $O_2$ concentration of 30% or more, an $O_2$ concentration of 35% or more, and an $O_2$ concentration of 40% or more. Examples of such a lower oxygen condition include an $O_2$ concentration of 10% or less, an $O_2$ concentration of 5% or less, an $O_2$ concentration of 4% or less, an $O_2$ concentration of 3% or less, an $O_2$ concentration of 2% or less, and an $O_2$ concentration of 1% or less.

Examples of the number of days for carrying out the step (i) of the present invention include, but are not particularly limited to, 3 days or more, 4 days or more, 5 days or more, 6 days or more, 7 days or more, and more days. The upper limit is not particularly limited, and it is, for example, 36 days or less, 30 days or less, 24 days or less, 18 days or less, or 12 days or less. The number of days for carrying out the step (i) of the present invention is more preferably 3 days or more and 12 days or less, and further preferably 6 days.

<Step (ii)>

The culture medium used in step (ii) of the present invention can be prepared by adding the aforementioned Wnt inhibitor and BMP inhibitor to a medium for the culture of animal cells, which is used as a basal medium. Examples of the basal medium include Glasgow's Minimal Essential Medium (GMEM), IMDM medium, Medium 199 medium, Eagle's Minimum Essential Medium (EMEM), αMEM medium, Dulbecco's modified Eagle's Medium (DMEM), Ham's F12 medium, RPMI 1640 medium, Fischer's medium, Neurobasal Medium (Invitrogen), and a mixed medium thereof. It is preferably a medium prepared by mixing DMEM and Ham's F12 medium at a mixing ratio of 1:1. The basal medium may comprise serum, or may comprise a serum replacement, instead of such serum. Examples of the serum replacement include albumin, transferrin, Knockout Serum Replacement (KSR) (a serum replacement for FBS used in the culture of ES cells), N2 supplement (Invitrogen), B27 supplement (Invitrogen), fatty acid, insulin, a collagen precursor, a trace element, and a combination of multiple substances selected from the aforementioned substances. The serum replacement is preferably KSR. When KSR is used in the step (ii) of the present invention, examples of the concentration of the KSR in the basal medium include 5%, 10%, 11%, 12%, 13%, 14%, 15%, 16%, 17%, 18%, 19%, and 20%. The concentration of KSR is preferably less than 20%, for example, 10% or more and 15% or less. The basal medium can also comprise one or more substances selected from 2-mercaptoethanol, 3'-thiol glycerol, lipid, amino acid, L-glutamine, Glutamax (Invitrogen), non-essential amino acid, vitamin, a growth factor, a low molecular weight compound, an antibiotic, an antioxidant, pyruvic acid, a buffer, inorganic salts, and the like. The preferred basal medium is a medium prepared by mixing DMEM comprising KSR, 2-mercaptoethanol, non-essential amino acid and L-glutamine with Ham's F12 medium at a mixing ratio of 1:1.

In the step (ii) of the present invention, the cells obtained in the step (i) may be used after they have been dissociated, or the cells may also be used directly. More preferably, a method of exchanging the culture medium comprising the cells obtained in the step (i) with a fresh one, and then continuing the culture, is applied. Thus, the culture in the step (ii) of the present invention is preferably carried out by a suspension culture.

With regard to the culture conditions applied in the step (i) of the present invention, the culture temperature is not particularly limited, and it is approximately 30° C. to 40° C., and preferably approximately 37° C. The culture is carried out under a $CO_2$-containing air atmosphere, and the $CO_2$ concentration is preferably approximately 2% to 5%. The $O_2$ concentration may be an $O_2$ concentration in an ordinary air, or it may be either a higher oxygen condition than usual, or a lower oxygen condition than usual.

Examples of the number of days for carrying out the step (ii) of the present invention include, but are not particularly limited to, 6 days or more, 7 days or more, 8 days or more, 9 days or more, 10 days or more, 11 days or more, 12 days or more, and more days. The upper limit is not particularly limited, and it is, for example, 48 days or less, 42 days or less, 36 days or less, 30 days or less, 24 days or less, or 18 days or less. The number of days for carrying out the step (ii) of the present invention is more preferably 6 days or more and 18 days or less, and further preferably 12 days.

<Step (iii)>

As a culture medium used in step (iii) of the present invention, a basal medium for the culture of animal cells can be used. Examples of the basal medium include Glasgow's Minimal Essential Medium (GMEM), IMDM medium, Medium 199 medium, Eagle's Minimum Essential Medium (EMEM), αMEM medium, Dulbecco's modified Eagle's Medium (DMEM), Ham's F12 medium, RPMI 1640 medium, Fischer's medium, Neurobasal Medium (Invitrogen), and a mixed medium thereof. The basal medium is preferably Neurobasal Medium. The basal medium may comprise serum, or may comprise a serum replacement, instead of such serum. Examples of the serum replacement include albumin, transferrin, Knockout Serum Replacement (KSR) (a serum replacement for FBS used in the culture of ES cells), N2 supplement (Invitrogen), B27 supplement (Invitrogen), fatty acid, insulin, a collagen precursor, a trace element, and a combination of multiple substances selected from the aforementioned substances. The serum replacement is preferably B27 supplement. The basal medium can also comprise one or more substances selected from 2-mercaptoethanol, 3'-thiol glycerol, lipid, amino acid, L-glutamine, Glutamax (Invitrogen), non-essential amino acid, vitamin, a growth factor, a low molecular weight compound, an antibiotic, an antioxidant, pyruvic acid, a buffer, inorganic salts, and the like. The preferred basal medium is Neurobasal Medium comprising B27 supplement and L-glutamine. As a culture medium used in the step (iii) of the present invention, a culture medium prepared by adding, for example, FGF8 (fibroblast growth factor 8), a neurotrophic factor and the like to the above-described basal medium, as appropriate, can be used.

In the present invention, FGF8 is not particularly limited. In the case of human FGF8, examples of the FGF8 include four splicing forms, namely, FGF8a, FGF8b, FGF8e and FGF8f. In the present invention, the FGF8 is more preferably FGF8b. Such FGF8 is commercially available, for example, from Wako Pure Chemical Industries, Ltd. or R & D systems, and it can be easily used. Alternatively, the FGF8 may also be obtained by allowing cells to forcibly express the FGF8 according to a method known to a person skilled in the art.

Examples of the concentration of FGF8 in the culture medium include 1 ng/mL, 5 ng/mL, 10 ng/mL, 50 ng/mL, 100 ng/mL, 150 ng/mL, 200 ng/mL, 250 ng/mL, 500 ng/mL, 1000 ng/mL, 2000 ng/mL, and 5000 ng/mL, but are not limited thereto. The concentration of FGF8 in the culture medium is preferably 100 ng/mL.

In the present invention, the neurotrophic factor is a ligand to a membrane receptor, which plays an important role in the survival of nerve cells and the function maintenance thereof. Examples of the neurotrophic factor include Nerve Growth Factor (NGF), Brain-derived Neurotrophic Factor (BDNF), neurotrophin 3 (NT-3), neurotrophin 4/5 (NT-4/5), neurotrophin 6 (NT-6), bFGF, acidic FGF, FGF-5, Epidermal Growth Factor (EGF), Hepatocyte Growth Factor (HGF), insulin, insulin-like growth factor 1 (IGF 1), insulin-like growth factor 2 (IGF 2), Glial cell line-derived Neurotrophic Factor (GDNF), TGF-b2, TGF-b3, interleukin 6 (IL-6), Ciliary Neurotrophic Factor (CNTF)), and LIF. The neurotrophic factor is commercially available, for example, from Wako Pure Chemical Industries, Ltd. or R & D systems, and it can be easily used. Alternatively, the neurotrophic factor may also be obtained by allowing cells to forcibly express the neurotrophic factor according to a method known to a person skilled in the art.

The step (iii) of the present invention is a step of culturing the cells obtained in the step (ii), and the culture may be either an adhesion culture or a suspension culture. When the adhesion culture is carried out, it can be carried out by culturing the cells using a culture vessel coated with an extracellular substrate. The coating treatment can be carried out by adding a solution containing such an extracellular substrate into a culture vessel and then removing the solution from the vessel, as appropriate.

In the present invention, the extracellular substrate is a supramolecular structure that is present outside of the cells. The extracellular substrate may be either a naturally-occurring product or an artificial product (recombinant). Examples of the extracellular substrate include substances such as polylysine, polyornithine, collagen, proteoglycan, fibronectin, hyaluronic acid, tenascin, entactin, elastin, fibrillin or laminin, and the fragments thereof. These extracellular substrates may be used in combination, or may also be products prepared from cells, such as BD Matrigel (registered trademark). The extracellular substrate is preferably a mixture of polyornithine, laminin and fibronectin.

In the step (iii) of the present invention, when the suspension culture is carried out, the culture can be carried out by appropriately replacing the culture medium comprising the cells obtained in the step (ii) with the culture medium used in the aforementioned step (iii) of the present invention. In the present invention, upon the replacement of the culture medium, the entire culture medium may be replaced, or for example, a half amount of the culture medium may be replaced over several times.

With regard to the culture conditions applied in the step (iii) of the present invention, the culture temperature is not particularly limited, and it is approximately 30° C. to 40° C., and preferably approximately 37° C. The culture is carried out under a $CO_2$-containing air atmosphere, and the $CO_2$ concentration is preferably approximately 2% to 5%. The $O_2$ concentration may be an $O_2$ concentration in an ordinary air, or it may be either a higher oxygen condition than usual, or a lower oxygen condition than usual.

From the viewpoint of obtaining cerebral cortex neurons, even if the culture is continued for a long period of time in the step (iii) of the present invention, there are no particular problems. Accordingly, it is not necessary to determine the upper limit of the number of days for carrying out the step (iii). Examples of the number of days for the step (iii) include 6 days or more, 7 days or more, 8 days or more, 9 days or more, 10 days or more, 11 days or more, 12 days or more, 14 days or more, 21 days or more, 28 days or more, 30 days or more, 35 days or more, and more days. It is more preferably 28 days or more, and further preferably for 28 days or 30 days.

<Cerebral Disorder Therapeutic Agent>

The cerebral cortex neurons obtained in the present invention can be administered as a preparation to patients with cerebral disorder. In the present invention, the cerebral disorder means a condition in which nerve cells are deleted by ischemia or the like, and an example of such cerebral disorder can be disorder occurring after cerebral infarction. The treatment of the cerebral disorder is carried out by suspending the cerebral cortex neurons produced by the above-described method in a normal saline or the like, and then transplanting the suspension into the nerve cell-deficient site of the patient. Accordingly, the present invention provides a cerebral disorder therapeutic agent comprising cerebral cortex neurons obtained from pluripotent stem cells by the above-described method, and preferably, a cerebral infarction therapeutic agent.

In the present invention, the number of cerebral cortex neurons comprised in a cerebral disorder therapeutic agent is not particularly limited, as long as a graft can adhere to a desired site after the administration thereof. For example, $15 \times 10^4$ or more of the cerebral cortex neurons may be comprised in a cerebral disorder therapeutic agent. In addition, the number of cerebral cortex neurons comprised in the cerebral disorder therapeutic agent may be adjusted, as appropriate, depending on symptoms or the size of a patient's body.

The cerebral cortex neurons can be transplanted into the affected site according to the method described, for example, in Nature Neuroscience, 2, 1137 (1999) or N Engl J Med.; 344: 710-9 (2001).

<Kit>

In another embodiment of the present invention, a kit for producing cerebral cortex neurons from pluripotent stem cells is included. This kit comprises culture media used in the aforementioned steps of producing cerebral cortex neurons, additives, culture vessels, etc. Examples of components comprised in the kit include reagents selected from the group consisting of a TGFβ inhibitor, bFGF, a Wnt inhibitor and a BMP inhibitor. The present kit may further comprise papers or instruction manuals, in which the procedures for the production steps are described.

Hereinafter, the present invention will be more specifically described in the following examples. However, needless to say, these examples are not intended to limit the scope of the present invention.

Example 1

Cells

Human ES cells (KhES-1) were obtained from Institute for Frontier Medical Sciences, Kyoto University (Suemori H, et al. Biochem Biophys Res Commun. 345: 926-32, 2006). The human iPS cells 404C2 are cells obtained by introducing Oct3/4, Sox2, Klf4, L-MYC, LIN28 and p53shRNA into human fibroblasts, using an episomal vector, and these cells were obtained from Professor Yamanaka et al. in Kyoto University (Okita, et al, Nat Methods. 8: 409-412, 2011). The human iPS cells 836B1 are cells obtained by introducing Oct3/4, Sox2, Klf4, L-MYC, LIN28, GLIS1 and p53shRNA into human fibroblasts, using an episomal vector, and these cells were obtained from Professor Yamanaka et al. in Kyoto University. The ES cells and the iPS cells were cultured on SNL cells (Takahashi K, et al, Cell. 131: 861-872, 2007).

Method for Inducing Differentiation of Cerebral Cortex

On the day before induction of differentiation, in order to separate the ES cells or the iPS cells, which had been cultured in a culture medium to which 10 μM Y-27632 (WAKO) had been added, from the SNL feeder cells, the SNL cells were removed with CTK and the remaining cells were then dissociated using Accumax (ICT). The cells were transferred on a 96-well plate (Lipidure-coat 96-well plate (NOF Corporation)) in an amount of $9 \times 10^3$ cells per well. Thereafter, the cells were subjected to a suspension culture in DMEM/F12 (WAKO) comprising 50 μM Y-27632 (WAKO), 10 μM SB43152 (Sigma), 10 ng/ml bFGF (Invitrogen), various types of Wnt inhibitors (DKK1 (R & D, 500 ng/ml), C59 (Cellagen Technology, 2-10 nM), XAV (Stemgent, 500 nM-2 μM) or IWP4 (Stemgent, 500 nM-2.5 μM)), LDN193189 (Stemgent), KSR (Invitrogen), 0.1 mM MEM non-essential amino acid (Invitrogen), 0.1 mM 2-mercaptoethanol (WAKO), and 2 mM L-Gln (Invitrogen) (initiation of differentiation induction, day 0). Three days after the initiation of differentiation induction, the medium was exchanged with the same medium as described above, which did not comprise Y-27632 (day 3). Three days later, the medium was exchanged with DMEM/F12 (WAKO) comprising various types of Wnt inhibitors (DKK1, C59, XAV or IWP4 (Stemgent)), LDN193189 (Stemgent), KSR (Invitrogen), 0.1 mM MEM non-essential amino acid (Invitrogen), 0.1 mM 2-mercaptoethanol (WAKO), and 2 mM L-Gln (Invitrogen) (day 6). Thereafter, the medium was exchanged with a fresh one of the same type every 3 days, and the culture was carried out for 18 days after the initiation of differentiation induction (day 18).

The obtained cell mass was transferred on a dish (24-well plate (BD)) coated with 50 μg/ml ornithine (Sigma), 5 μg/ml laminin (Sigma) and 5 μg/ml fibronectin (BD Bioscience Pharmingen), and the culture was continued in Neurobasal (Invitrogen), to which B27 (Invitrogen), 2 mM L-Gln, and 10 units/ml penicillin and streptomycin (Invitrogen) had been added. The culture was carried out for, at maximum, 46 days after the initiation of differentiation induction. It is to be noted that the medium was exchanged with a fresh one every 2 or 3 days. The protocols for the induction step are shown in FIG. 1.

Studies of Wnt Inhibitors

Figure 2:
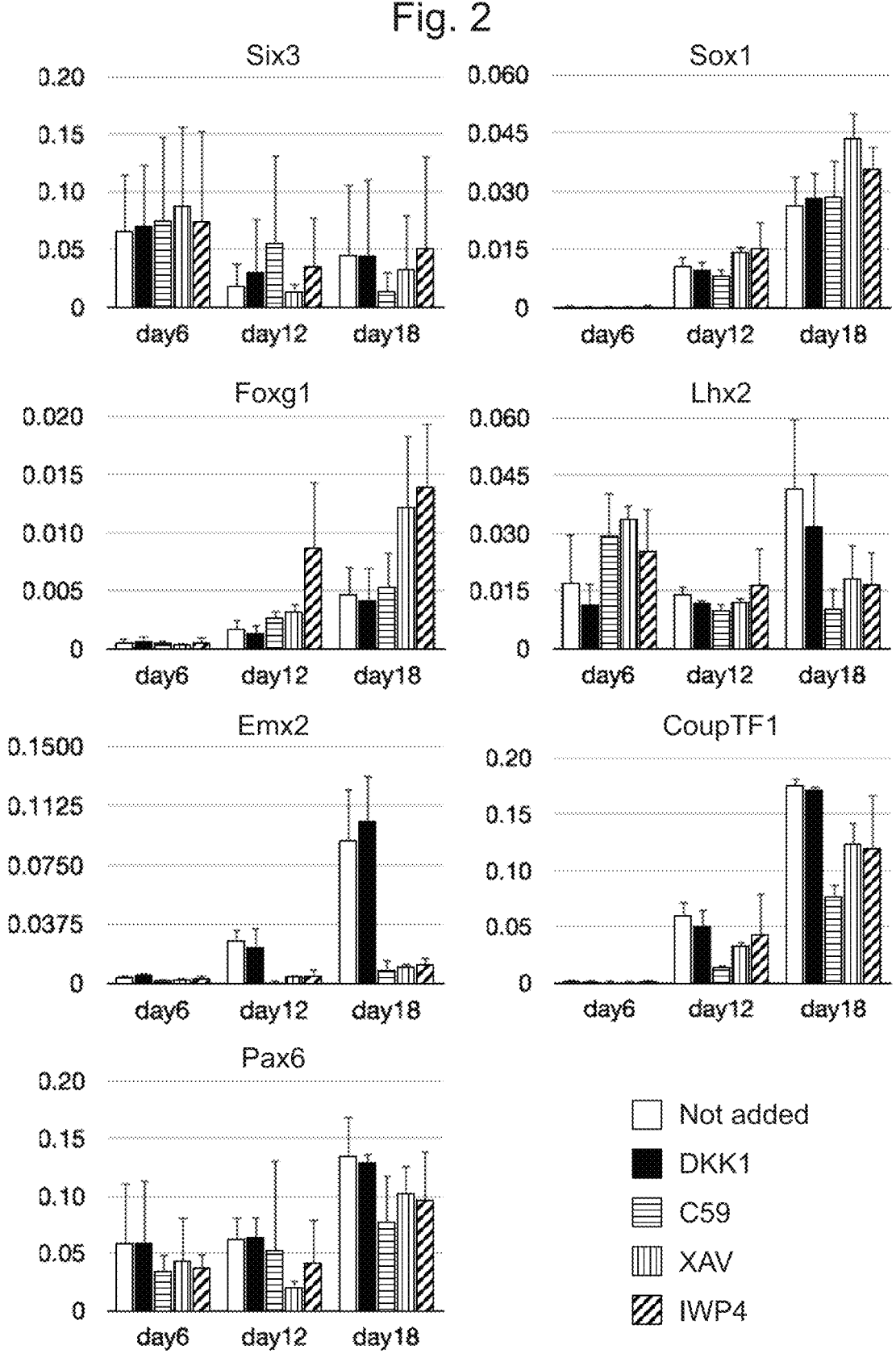
FIG. 2 includes graphs showing the expression levels of Six3, Sox1, Foxg1, Lhx2, Emx2, CoupTF1 and Pax6 in cells on the 6th day (day 6), 12th (day 12) and 18th day (day 18) of culture, in the case of using DKK1, C59, XAV or IWP4 as a Wnt inhibitor. In the figure, the term "Not added" means the results in the case of using no Wnt inhibitors.

In the above-described induction method, 500 ng/ml DKK1, 2 nM C59, 500 nM XAV or 500 nM IWP4 was added as a Wnt inhibitor to the cells, and the obtained mixture was then cultured for 18 days. Thereafter, the expression levels of Six3 (forebrain marker), Sox1 (neuroectodermal marker), Foxg1 (cerebral cortex-forming factor), Lhx2 (cerebral cortex-forming factor), Emx2 (forebrain back portion marker), CoupTF1 (forebrain back portion marker) and Pax6 (forebrain front portion marker) genes in the cultured cells were measured by a qPCR method (FIG. 2). As a result, it was found that when DKK1 was used as a Wnt inhibitor, the expression levels of Emx2 and CoupTF1 were high, and that a large number of cells in the back portion of the forebrain were induced.

Moreover, the cells, to which 500 ng/ml DKK1, 2 nM C59 or 500 nM XAV had been added as a Wnt inhibitor, and which had been then cultured by the above-described induction method for 46 days, were subjected to immunostaining of using antibodies against CoupTF1 and Ctip2 as a marker for the phase V of cerebral cortex neurons. As a result, it was confirmed that when C59 was used, a large number of CoupTF1-negative Ctip2-positive cerebral cortex neurons were induced (FIG. 3).

From the aforementioned results, it was suggested that C59 can be preferably used as a Wnt inhibitor.

Studies of C59 Concentration

The concentration of C59 used as a Wnt inhibitor in the above-described induction method was examined. Specifically, without using C59, or using 2.5 nM, 10 nM and 1 μM C59, the cells were cultured for 18 days. When 1 μM C59 was used, no spheres were formed in the suspension culture, and thus, the subsequent analysis was not carried out. The obtained spheres were subjected to immunostaining of using an antibody against Pax6. As a result, positive cells were confirmed under all conditions (FIG. 4A). Furthermore, the expression levels of the Foxg1, Lhx2, Emx2 and CoupTF1 genes in the obtained spheres were measured according to a qPCR method (FIG. 4B). As a result, the expression level of CoupTF1 was low and the expression levels of Lhx2 and Foxg1 were high in the case of using 10 nM C59. Thus, it could be confirmed that the conditions were optimal. However, when the ES cells (Kh-1) were used, the spheres obtained in the case of using 10 nM C59 did not adhere so much to an OFL coat dish. Accordingly, it was suggested that there may also be a case where a concentration of lower than 10 nM is appropriate. Therefore in the subsequent analyses, 2 nM C59 was to be used as a Wnt inhibitor.

Studies of LDN193189 Concentration

The concentration of LDN193189 used in the above-described induction method was examined. Specifically, using 0.1 μM, 0.5 μM and 2 μM LDN193189, the cells were cultured for 46 days. The obtained cells were subjected to immunostaining of using antibodies against CoupTF1 and Ctip2. As a result, it was confirmed that CoupTF1-negative Ctip2-positive cells were obtained in a concentration-dependent manner (FIGS. 5A and B). Furthermore, the expression levels of the CoupTF1 and Sfrp1 genes were measured according to a qPCR method (FIG. 5C). As a result, it was confirmed that cells, in which the expression level of CoupTF1 was low and the expression level of Sfrp1 was high, were obtained in a concentration-dependent manner. However, when 2 μM LDN193189 was used, cell death was often found in spheres obtained on the 18th day of the culture. Thus, it was confirmed that cytotoxicity also strongly appeared. Accordingly, it was suggested that LDN193189 having a concentration of lower than 2 μM was suitable, taking into consideration the subsequent operations. Therefore, in the subsequent analyses, LDN193189 with a concentration of 0.1 μM or 0.5 μM was to be used.

Studies of KSR Concentration

The concentration of KSR used in the above-described induction method was examined. Specifically, using 10%, 15% and 20% KSR, the cells were cultured for 46 days. The obtained cells were subjected to immunostaining of using antibodies against CoupTF1 and Ctip2. As a result, it was confirmed that CoupTF1-negative Ctip2-positive cells were decreased in a concentration-dependent manner (FIGS. 6A and B). Furthermore, the expression levels of the CoupTF1 and Sfrp1 genes were measured according to a qPCR method (FIG. 6C). As a result, it was confirmed that cells, in which the expression level of CoupTF1 was high and the expression level of Sfrp1 was low, were obtained in a concentration-dependent manner. Accordingly, it was suggested that KSR having a concentration of lower than 20% is suitable for induction of the cerebral cortex neurons in the front portion of the cerebral cortex. In the subsequent analyses, 10% or 15% KSR was to be used.

Studies of Replacement of SB431542

The concentration of A-83-01 used as a replacement of SB431542 in the above-described induction method was examined. Specifically, using 0.5 μM, 2 μM or 5 μM A-83-01 (WAKO), the cells were cultured for 46 days. The obtained cells were subjected to immunostaining of using antibodies against CoupTF1 and Ctip2. As a result, it was confirmed that CoupTF1-negative Ctip2-positive cells were obtained, as in the case of SB431542 (FIG. 7). In addition, in the concentration range of the examined A-83-01, there was not found a large difference in the induction efficiency of cerebral cortex neurons.

Effects of Transplantation

Figure 8:
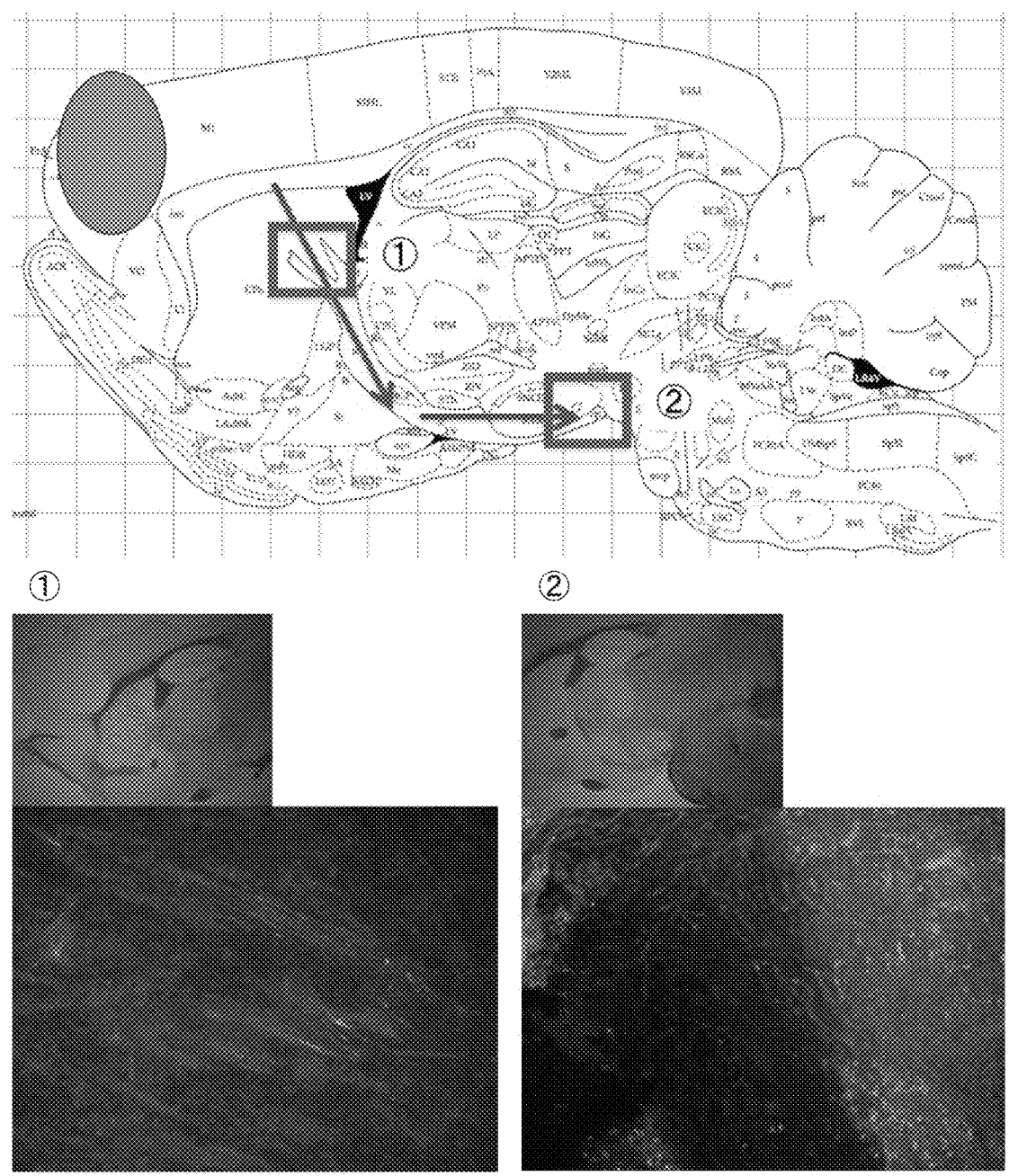
FIG. 8 shows a schematic view of mouse brain (upper view), and the immunostained images of cells in individual sites to human NCAM, which are obtained 6 months after transplantation of the cells induced by the method of the present invention into the mouse motor area (lower views). The region surrounded with the circle in the upper view shows the site into which the cells have been transplanted, and the immune tissues indicated with number 1 or 2 in the upper view are shown in the lower views. In the immunostained images, the staining of human cells derived from the transplanted cells is shown.
Figure 9:
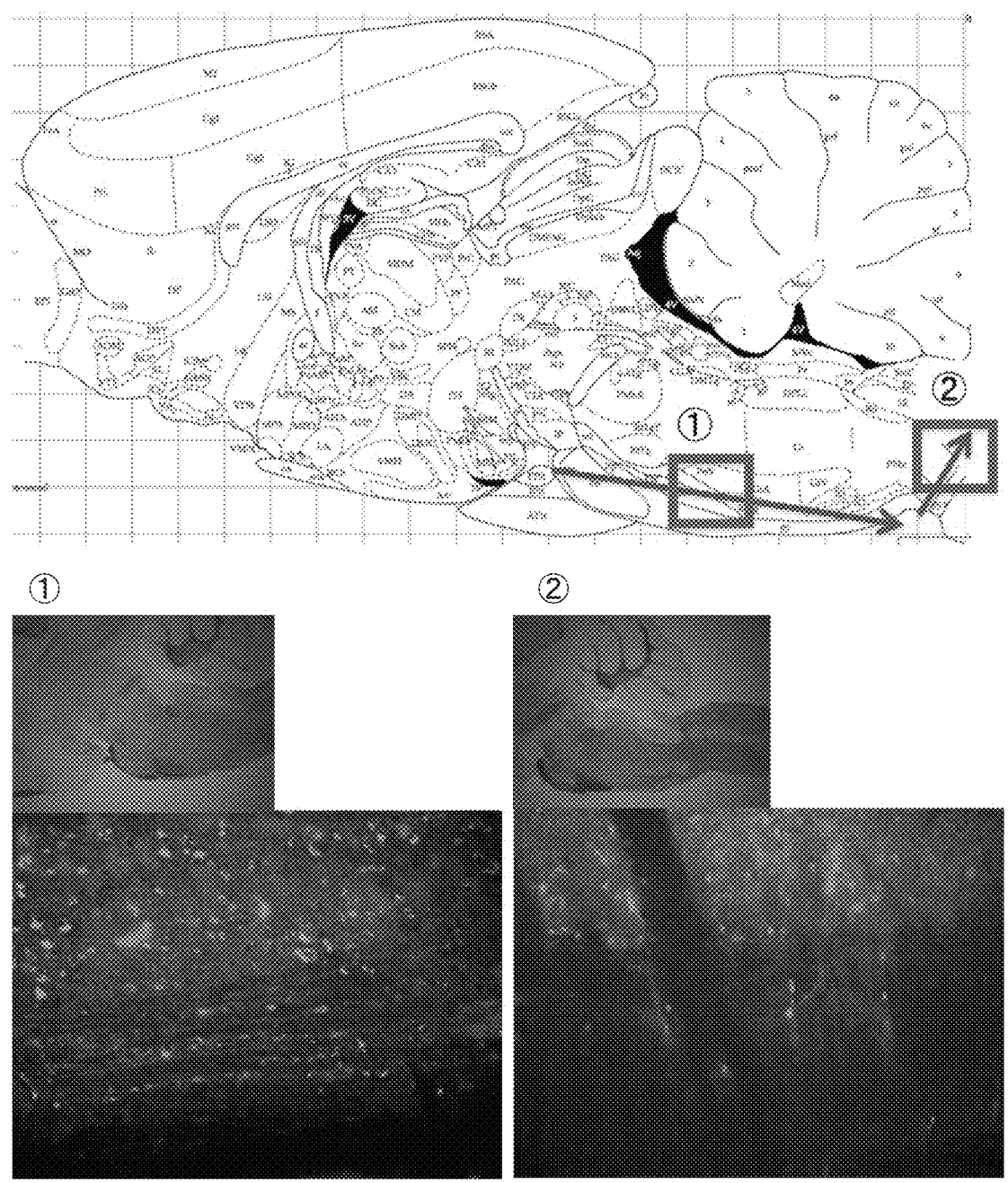
FIG. 9 shows a schematic view of mouse brain (upper view), and the immunostained images of cells in individual sites to human NCAM, which are obtained 6 months after transplantation of the cells induced by the method of the present invention into the mouse motor area (lower views). The immune tissues indicated with number 1 or 2 in the upper view are shown in the lower views. In the immunostained images, the staining of human cells derived from the transplanted cells is shown.

Cerebral cortex neurons, which had been induced by the above-described method for 48 days, were suspended in PBS, and the obtained suspension was then transplanted into the corticocerebral motor area of a mouse. On the 6th month after the transplantation, the excised brain section was immunostained with a human NCAM antibody (Santa Cruz), and was then analyzed. As a result, it was confirmed that axon derived from the transplanted cells extended to the midbrain, bridge, and medulla oblongata, and that the axon then reached the spinal cord through the corticospinal tract (FIGS. 8 to 10).

Example 2

Culture of iPS Cells

The iPS cells (836B1) were cultured according to the method described in Miyazaki T et al., Nat Commun. 3:

1236, 2012. Briefly, the iPS cells were cultured on a 6-well plate coated with Laminin 511E8.

Modification of Method of Inducing Differentiation of Cerebral Cortex

The iPS cells (836B1) were dissociated using Accumax, and were then transferred on a 96-well plate (Lipidure-coat 96-well plate) in an amount of $9\times10^3$ cells per well. Thereafter, the cells were subjected to a suspension culture in DMEM/F12 comprising 50 µM Y-27632, 10 µM SB43152, 10 ng/ml bFGF, 50 nM C59, 0.1 µM LDN193189, 10% KSR, 0.1 mM MEM non-essential amino acid, 0.1 mM 2-mercaptoethanol, and 2 mM L-Gln (initiation of differentiation induction, day 0). Three days after the initiation of differentiation induction, the medium was exchanged with the same medium as described above, which did not comprise Y-27632 (day 3). Three days later, the medium was exchanged with DMEM/F12 comprising 50 nM C59, 0.1 µM LDN193189, 10% KSR, 0.1 mM MEM non-essential amino acid, 0.1 mM 2-mercaptoethanol, and 2 mM L-Gln (day 6). Thereafter, the medium was exchanged with a fresh one of the same type every 3 days, and the culture was carried out for 18 days after the initiation of differentiation induction (day 18).

The obtained cell mass was transferred on a dish (24-well plate) coated with 50 µg/ml ornithine, 5 µg/ml laminin and 5 µg/ml fibronectin, and the culture was then continued in Neurobasal, to which B27, 2 mM L-Gln, and 10 units/ml penicillin and streptomycin had been added, until the 48th day after the initiation of differentiation induction. It is to be noted that the medium was exchanged with a fresh one every 3 or 4 days.

Figure 11:
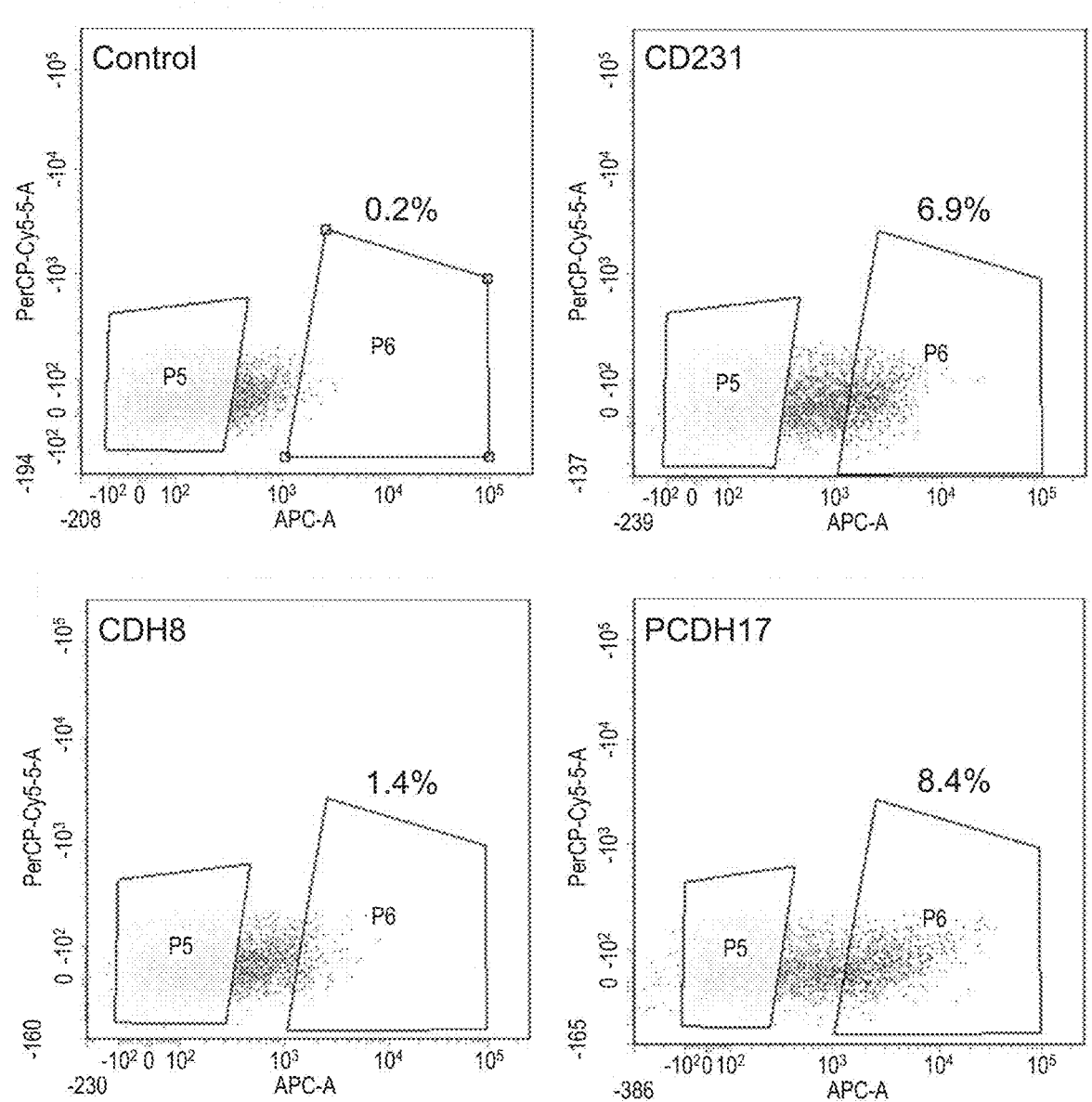
FIG. 11 shows the results obtained by analyzing the cells on day 48 of differentiation induction using a flow cytometer. The upper left view shows the results of a negative control, the upper right view shows the results obtained by staining the cells with a CD231 antibody, the lower left view shows the results obtained by staining the cells with a CDH8 antibody, and the lower right view shows the results obtained by staining the cells with a PCDH17 antibody. The horizontal axis indicates fluorescence intensity. In the figure, the content rate of each marker-positive cells is shown with a numerical value.

The aforementioned cells on the 48th day of the differentiation induction were dissociated using Accumax, and were then labeled using an anti-CD231 antibody (Thermo), an anti-CDH8 antibody (Antibodies) or an anti-PCDH17 antibody (Thermo). Thereafter, the labeled cells were analyzed using FACS (FIG. 11). It was confirmed that the cells after completion of the induction comprised cells positive to CD231, CDH8 or PCDH17, at a percentage of 6.9%, 1.4% or 8.4%, respectively.

Subsequently, the CD231-, CDH8- or PCDH17-positive cells were recovered, and were then transferred on a 96-well plate (Lipidure-coat 96-well plate) in an amount of $1\times10^4$ cells per well. Thereafter, the cells were cultured for 3 days in Neurobasal, to which B27, 2 mM L-Gln, 10 units/ml penicillin and streptomycin, and 10 µM Y-27632 had been added, and then, were further cultured for 11 days in the same medium as described above, from which Y-27632 was removed. After completion of the culture, the cells were immunostained with antibodies against CoupTF1 and Ctip2. As a result, many Ctip2-positive cells were found in CD231-, CDH8- or PCDH17-positive cells (FIG. 12A). Moreover, it was also confirmed that many CoupTF1-negative Ctip2-positive cells were comprised in the CD231-, CDH8- or PCDH17-positive cells. From the aforementioned results, it was suggested that it is likely that nerve cells existing in the corticocerebral motor area can be concentrated by extracting the CD231-, CDH8- or PCDH17-positive cells from the cells inducted by the above-described method.

Example 3

Modification of Method of Inducing Differentiation of Cerebral Cortex

The iPS cells (836B1), which had been cultured using Laminin 511E8 under feeder-free conditions, were dissociated using Accumax, and were then transferred on a 96-well plate (Lipidure-coat 96-well plate) in an amount of $9\times10^3$ cells per well. Thereafter, the cells were subjected to a suspension culture in DMEM/F12 comprising 50 µM Y-27632, 10 µM SB43152, 10 ng/ml bFGF, 10 nM-50 nM C59, 0.1 µM LDN193189, 10% KSR, 0.1 mM MEM non-essential amino acid, 0.1 mM 2-mercaptoethanol, and 2 mM L-Gln (initiation of differentiation induction, day 0). Three days after the initiation of differentiation induction, the medium was exchanged with the same medium as described above, which did not comprise Y-27632 (day 3). Three days later, the medium was exchanged with DMEM/F12 comprising 10 nM-50 nM C59, 0.1 µM LDN193189, 10% KSR, 0.1 mM MEM non-essential amino acid, 0.1 mM 2-mercaptoethanol, and 2 mM L-Gln (day 6). Thereafter, the medium was exchanged with a fresh one of the same type every 3 days, and the culture was carried out for 18 days after the initiation of differentiation induction (day 18).

A half of the medium on day 18 was removed by aspiration, and thereafter, Neurobasal, to which B27, 2 mM L-Gln, and 10 units/ml penicillin and streptomycin had been added, was added in the same amount as the removed medium to the remaining medium. Likewise, a half amount of the medium was exchanged on day 21. On day 24, the cells were transferred on a petri dish, and thereafter, a half of the medium was exchanged every 3 or 4 days. On day 46, the obtained cells were immunostained using antibodies against CoupTF1 and Ctip2. As a result, there was not found a large difference between the present cells and the cells obtained in Examples 1 or 2, in terms of the expression of CoupTF1 and Ctip2 (FIGS. 13A and B). From the aforementioned results, it was confirmed that nerve cells existing in the desired corticocerebral motor area can be induced by the suspension culture even after day 18.

Example 4

Modification of Method of Inducing Differentiation of Cerebral Cortex

On the day before induction of differentiation, in order to separate the iPS cells (836B1), which had been cultured in a culture medium to which 10 µM Y-27632 had been added, from the SNL feeder cells, the SNL cells were removed with CTK and the remaining cells were then dissociated using Accumax. The cells were transferred on a 96-well plate (Lipidure-coat 96-well plate) in an amount of $9\times10^3$ cells per well. Thereafter, the cells were subjected to a suspension culture in DMEM/F12 comprising 50 µM Y-27632, 10 µM SB43152, 10 ng/ml bFGF, various types of Wnt inhibitors (50 nM C59, 100 nM LGK-974, or 1 µM ICG-001 (Cellagen Technology)), 100 nM LDN193189, 10% KSR, 0.1 mM MEM non-essential amino acid, 0.1 mM 2-mercaptoethanol, and 2 mM L-Gln (initiation of differentiation induction, day 0). Three days after the initiation of differentiation induction, the medium was exchanged with the same medium as described above, which did not comprise Y-27632 (day 3). Three days later, the medium was exchanged with DMEM/F12 comprising various types of WNT inhibitors (C59, LGK-974, or ICG-001), 100 nM LDN193189, 10% KSR, 0.1 mM MEM non-essential amino acid, 0.1 mM 2-mercaptoethanol, and 2 mM L-Gln (day 6). Thereafter, the medium was exchanged with a fresh one of the same type every 3 days, and the culture was carried out for 18 days after the initiation of differentiation induction (day 18).

A half of the medium on day 18 was removed by aspiration, and thereafter, Neurobasal, to which B27, 2 mM L-Gln, and 10 units/ml penicillin and streptomycin had been added, was added in the same amount as the removed medium to the remaining medium. Likewise, a half amount of the medium was exchanged on day 21. On day 24, the cells were transferred on a petri dish, and thereafter, a half of the medium was exchanged every 3 or 4 days. On day 46, the obtained cells were immunostained using antibodies against CoupTF1 and Ctip2. As a result, there was not found a large difference between the present cells and the cells obtained in Examples 1 or 2, in terms of the expression of Ctip2 (FIGS. 14A and B). In addition, there was not found a large difference between C59 and LGK-974 having a similar action to C59, in terms of the efficiency of inducing CoupTF1-negative Ctip2-positive cells, but such induction efficiency was significantly low in ICG-001 having a different action to C59 (FIG. 14C). From the aforementioned results, it was confirmed that nerve cells existing in the desired corticocerebral motor area can be induced even by utilizing the WNT inhibitor LGK-974 having a similar action to C59.

INDUSTRIAL APPLICABILITY

The present invention is useful for regenerative medicine, in particular, for the treatment of damaged brain such as cerebral ischemia.

All publications, patents and patent applications cited herein are incorporated in the present description by reference in their entirety.

The invention claimed is:

1. A method for producing cerebral cortex neurons from pluripotent stem cells, comprising the following steps:
 (i) a step of performing a suspension culture of pluripotent stem cells in a culture medium containing a TGFβ inhibitor, bFGF, a Wnt inhibitor, and a BMP inhibitor,
 (ii) a step of performing a suspension culture of the cells obtained in the step (i) in a culture medium containing a Wnt inhibitor and a BMP inhibitor, and
 (iii) a step of culturing the cells obtained in the step (ii), and
 (iv) a step of extracting from the cultured cells, the cells which are positive for at least one marker protein selected from the group consisting of CD231, PCDH17 and CDH8, after completion of the step (iii).

2. The method according to claim 1, wherein the pluripotent stem cells are human pluripotent stem cells.

3. The method according to claim 2, wherein the human pluripotent stem cells are human iPS cells or human ES cells.

4. The method according to claim 1, wherein the TGFβ inhibitor is SB431542 or A-83-01.

5. The method according to claim 1, wherein the Wnt inhibitor is a PORCN inhibitor.

6. The method according to claim 1, wherein the Wnt inhibitor is C59 or LGK-974.

7. The method according to claim 1, wherein the BMP inhibitor is LDN193189.

8. The method according to claim 1, where the culture medium of steps (i) and (ii) further contain serum or a serum replacement.

9. The method according to claim 1, wherein the culture medium of the step (i) further contains a ROCK inhibitor.

10. The method according to claim 1, wherein the produced cerebral cortex neurons are nerve cells that are equivalent to nerve cells in the corticocerebral motor area of a brain, in that they are positive for Ctip2 and negative for CoupTF1.

11. The method according to claim 1, wherein the step (i) is carried out for at least 3 days.

12. The method according to claim 1, wherein the step (ii) is carried out for at least 6 days.

* * * * *